US007091046B2

(12) United States Patent
Monforte

(10) Patent No.: US 7,091,046 B2
(45) Date of Patent: Aug. 15, 2006

(54) MULTIPLEXED PROTEIN EXPRESSION AND ACTIVITY ASSAY

(75) Inventor: Joseph A. Monforte, Berkeley, CA (US)

(73) Assignee: HK Pharmaceuticals, Inc., San Diego, CA (US)

( * ) Notice: Subject to any disclaimer, the term of this patent is extended or adjusted under 35 U.S.C. 154(b) by 419 days.

(21) Appl. No.: 10/014,731

(22) Filed: Dec. 11, 2001

(65) Prior Publication Data

US 2006/0110723 A1 May 25, 2006

Related U.S. Application Data

(60) Provisional application No. 60/254,958, filed on Dec. 11, 2000.

(51) Int. Cl.
G01N 24/00 (2006.01)
(52) U.S. Cl. ............ 436/173; 436/518; 436/523; 436/802; 435/6; 435/7.1; 435/973
(58) Field of Classification Search ............ 435/5, 435/6, 7.1, 7.92–7.94, 235.1, 973; 436/501, 436/518, 802, 523, 164, 172, 173
See application file for complete search history.

(56) References Cited

U.S. PATENT DOCUMENTS

| 4,683,202 | A | | 7/1987 | Mullis .................... 435/91 |
| 4,797,363 | A | * | 1/1989 | Teodorescu et al. ..... 435/235.1 |
| 5,223,408 | A | | 6/1993 | Goeddel et al. ........... 435/69.3 |
| 5,223,409 | A | | 6/1993 | Ladner et al. ............. 435/69.7 |
| 5,288,622 | A | | 2/1994 | Gray et al. ................ 435/69.4 |
| 5,316,922 | A | | 5/1994 | Brown et al. ............. 435/69.7 |
| 5,348,867 | A | | 9/1994 | Georgiou et al. .......... 435/69.7 |
| 5,395,750 | A | | 3/1995 | Dillon et al. ................ 435/5 |
| 5,403,484 | A | | 4/1995 | Ladner et al. ........... 435/235.1 |
| 5,665,539 | A | * | 9/1997 | Sano et al. .................. 435/6 |
| 5,741,668 | A | * | 4/1998 | Ward et al. .............. 435/69.1 |
| 5,837,500 | A | * | 11/1998 | Ladner et al. ............. 435/69.7 |
| 5,864,137 | A | | 1/1999 | Becker et al. ............. 250/287 |
| 5,866,344 | A | * | 2/1999 | Georgiou .................. 435/7.21 |
| 5,939,272 | A | * | 8/1999 | Buechler et al. ............ 435/7.1 |
| 5,965,363 | A | | 10/1999 | Monforte et al. ............. 435/6 |
| 6,051,378 | A | | 4/2000 | Monforte et al. ............. 435/6 |
| 6,090,558 | A | | 7/2000 | Butler et al. ................. 435/6 |
| 6,104,028 | A | | 8/2000 | Hunter et al. ............. 250/288 |
| 6,232,107 | B1 | | 5/2001 | Bryan et al. ............... 435/189 |
| 6,472,146 | B1 | * | 10/2002 | Larocca et al. .............. 435/5 |
| 6,686,154 | B1 | * | 2/2004 | Nock et al. ................... 435/6 |
| 2002/0076727 | A1 | * | 6/2002 | Cardone et al. ............. 435/7.1 |
| 2002/0142354 | A1 | * | 10/2002 | Wildsmith et al. ........... 435/7.2 |
| 2002/0187464 | A1 | * | 12/2002 | Klempner et al. ............. 435/5 |
| 2004/0142493 | A1 | * | 7/2004 | Hutchens et al. ........... 436/518 |

FOREIGN PATENT DOCUMENTS

| GB | WO 97/44491 | * | 11/1997 |
| WO | 9910485 | | 3/1999 |
| WO | 9956129 | | 11/1999 |
| WO | 0029555 | | 5/2000 |
| WO | 0123619 | | 4/2001 |
| WO | 0184154 | | 11/2001 |
| WO | 0194950 | | 12/2001 |
| WO | 0239120 A1 | | 5/2002 |

OTHER PUBLICATIONS

Arnheim et al., "Polymerase Chain Reaction", *C&EN*, pp. 36-47, 1990.
Arnott et al., "An Integrated Approach to Proteone Analysis: Identification of Proteins Associated with Cardiac Hyperthophy", *Anal. Biochem.*, 258:1-18, 1998.
Barringer et al., "Blunt-End and Single-Strand Ligations by *Escherichia coli* Ligase: Influence on an in vitro Amplification", *Gene*, 89:117-122, 1990.
Black et al., "Random Sequence Mutagenesis for the Generation of Active Enzymes", *Methods in Mol. Biol.*, 57:335-349, 1996.
Boublik et al., "Eukaryotic Virus Display: Engineering the Major Surface Glycoprotein of the *Autographa californica* Nuclear Polyhedrosis Virus (AcNPV) for the Presentation of Foreign Proteins on the Virus Surface", *Biotechnology*, 13:1079-1084, 1995.
Bruchez et al., "Semiconductor Nanocrystals as Fluorescent Biological Label", *Science*, 281:2013-2016, 1998.
Burritt et al., "Filamentous Phage Display of Oligopeptide Libraries", *Anal. Biochem.*, 238:1-13, 1996.
Celis et al., "2D Protein Electrophoresis: Can It Be Perfected?", *Curr. Opin. Biotechnol.*, 10:16-21, 1999.
Chee et al., "Accessing Genetic Information with High-Density DNA Arrays", *Science*, 274:610-614, 1996.
Chiswell et al., "Phage Antibodies: Will New 'Coliclonal' Antibodies Replace Monoclonal Antibodies?", *Trends Biotechnol.*, 10:80-84, 1992.
Clackson et al., "Making Antibody Fragments Using Phage Display Libraries", *Nature*, 352:624-628, 1991.
Easterling et al., "Monitoring Protein Expression in Whole Bacterial Cells with MALDI Time-of-Flight Mass Spectrometry", *Anal. Chem.*, 70(13):2704-2709, 1998.
Fannon, M., "Gene Expression in Nomrala nd Disease States—Identification of Therapeutic Targets", *Trends Biotechnol.*, 14:294-298, 1996.
Filippini et al., "A Novel Flow Cytometric Method for the Quantification of p53 Gene Expression", *Cytometry*, 31;180-186, 1998.
Fodor, S., "Massively Parallel Genomics", *Science*, 277:393-395, 1997.
Fodor, S., "Genes, Chips, and the Human Genome", *FASEB Journal*, 11:A879, 1997.
Fu et al., "Isolation for Phage Display Libraries of Single Chain Variable Fragment Antibodies that Recognize Conformational Epitopes in the Malaria Vaccine Candidate, Apical Membrane Antigen-1", *J. Biol. Chem.*, 272(41):25678-25684, 1997.

(Continued)

*Primary Examiner*—Long V. Le
*Assistant Examiner*—Gary W. Counts
(74) *Attorney, Agent, or Firm*—Fish & Richardson P.C.; Stephanie Seidman

(57) ABSTRACT

A system for analyzing expression levels and activity of a plurality of proteins is provided. A bio-displayed polypeptide binding component associated with a predetermined marker is used to bind the proteins of interest. The predetermined marker components are then amplified and detected in a high throughput manner.

24 Claims, 1 Drawing Sheet

OTHER PUBLICATIONS

Garden et al., "Excess Salt Removal with Matrix Rinsing: Direct Peptide Profiling of Neurons from Marine Invertebrates Using Matrix-Assisted Laser Desorption/Ionization Time-of-Flight Mass Spectrometry", *J. Mass Spectrom.*, 31:1126-1130, 1996.
Glaser et al., "Antibody Engineering by Codon-Based Mutagenesis in a Filamentous Phage Vector System", *J. Immunol.*, 149(12):3903-3913, 1992.
Gonzalez et al., "Intracellular Detection Assays for High-Throughput Screening", *Curr. Opin. Biotechnol.*, 9:624-631, 1998.
Griffiths et al., "Isolation of High Affinity Human Antibodies Directly from Large Synthetic Repertoires", *EMBO J.*, 13(14):3245-3260, 1994.
Guatelli et al., "Isothermal, in vitro Amplification of Nucleic Acids by a Multienzyme Reaction Modeled After Retroviral Replication", *Proc. Natl. Acad. Sci. USA*, 87:1874-1878, 1990.
Hawkins et al., "A Magnetic Attraction to High-Throughput Genomics", *Science*, 276:1887-1889, 1997.
Hill et al., "Phage Presentation", *Mol. Biol.*, 20(4):685-692, 1996.
Hoffman et al., Expression of Fully Functional Tetrameric Human Hemoglobin in *Escherichia coli*, *Proc. Natl. Acad. Sci. USA*, 87:8521-8525, 1990.
Hoogenboom et al., "Mutli-Subunit Proteins on the Surface of Filamentous Phage: Methologies for Displaying Antibody (Fab) Heavy and Light Chains", *Nucl. Acids Res.*, 19(15):4133-4137, 1991.
Houston et al., "The Chemical-Biological Interface: Developments in Automated and Miniaturised Screening Technology", *Curr. Opin. Biotechnol.*, 8:734-740, 1997.
Houston et al., "Rapid Analysis of Hemoglobin from Whole Human Blood by Matrix-Assisted Laser Desorption/Ionization Time-of-Flight Mass Spectrometry", *Rapid Commun. Mass Spectrom.*, 1:1435-1439, 1997.
Huse et al., "Generation of a Large Combinatorial Library of the Immunoglobin Repertoire in Phage Lambda", *Science*, 246:1275-1281, 1989.
IUPAC-IUB Commission on Biochemical Nomenclature Symbols for Amino-Acid Derivatives and Peptides Recommendations (1971), *Biochem.*, 11:942-944, 1972.
IUPAC-IUB Combined Commission on Biochemical Nomenclature Abbreviated Nonemclature of Synthetic Polypeptides (Polymerized Amino Acids)$^{1-3}$ Tentative Rules, *J. Biol. Chem.*, 243(10):2451-2453, 1968.
Jessen et al., "Production of Human Hemoglobin in *Escherichia coli* Using Cleavable Fusion Protein Expression Vector", *Methods Enzymol.*, 231:347-364, 1994.
Jimenez et al., "Ultramicroanalysis of Peptide Profiles in Biological Samples Using MALDI Mass Spectrometry", *Exp Nephrol.*, 6:421-428, 1998.
*Kirk-Othmer Encyclopedia of Chemical Technology*, vol. 5, Fourth Edition, pp. 1071-1094.
Kohler et al., "Continuous Cultures of Fused Cells Secretin Antibody of Predefined Specificity", *Nature*, 256:495-497, 1975.
Kozian et al., "Comparative Gene-Expression Analysis", *Trends Biotechnol.*, 17:73-78, 1999.
Kwoh et al., "Transcription-based Amplification System and Detection of Amplified Human Immunodeficiency Virus Type 1 with a Bead-Based Sandwich Hybridization Format", *Proc. Natl. Acad. Sci. USA*, 86:1173-1177, 1989.
Landegren et al., "A Ligase-Mediated Gene Detection Technique", *Science*, 241:1077-1080, 1988.
Li et al., "Detection Limits for Matrix-assisted Laser Desorption of Polypeptides with an External Ion Source Fourier-transform Mass Spectrometer", *Rapid Commun. Mass Spectrom.*, 8:743-749, 1994.
Lomelli et al., "Quantitative Assays Based on the Use of Replicable Hybridization Probes", *Clin. Chem.*, 35(9):1826-1831, 1989.
Lowman, H.B., "Bacteriophage Display and Discovery of Peptide Leads for Drug Development", *Annu. Rev. Biophys. Biomol. Struct.*, 26:401-424, 1997.
Methods and Materials: Amplification of Nucleic Acid Sequences: The Choices Multiply, *The Journal of NIH Research*, 3:81-86, 1991.
Nicola et al., "Application of the Fast-evaporation Sample Preparation Method for Improving Quantification of Angiotensin II by Matrix-assisted Laser Desorption/Ionization", *Rapid Commun. Mass Spectrom.*, 9:1164-1171, 1995.
Opitek et al., "Comprehensive Two-Dimensional High-Performance Liquid Chromatography for the Isolation of Overexpressed Proteins and Proteone Mapping", *Ana. Biochem.*, 258:349-361, 1998.
Parmley et al., "Antibody-selectable Filamentous fd Phage Vectors: Affinity Purification of Target Genes", *Gene*, 73:305-318, 1988.
Persic et al., "Single-chain Variable Fragments Selected on the 57-76 p21R as Neutralising Epitope from Phage Antibody Libraries Recognise the Parental Protein", *FEBS Lett.*, 443:112-116, 1999.
Rivera et al., "A Solid-Phase Fluorescent Immunoassay for Detecting Canine or Mink Enteritis Parvoriruses in Faecal Samples", *Veter. Microbiol.*, 15:1-9, 1987.
Rodi et al., "Phase-display Technology—Finding a Needle in a Vast Molecular Haystack", *Curr. Opin. Biotechnol.*, 10:87-93, 1987.
Sambrook et al., "Molecular Cloning, A Laboratory Manual", Cold Spring Harbor Laboratory Press, Chapter 8, vol. 3, p. B.13, 1989.
Sarubbi et al., "A Cell-Free, Nonisotopic, High-Throughput Assay for Inhibitors of Type-I Interleukin-1 Receptor", *Anal. Biochem.*, 237:70-75, 1996.
Shen et al., "Production of Unmodified Human Adult Hemoglobin in *Escherichia coli*", *Proc. Natl., Acad. Sci. USA*90:8108-8112, 1993.
Smith et al., "Single-step Purification of Polypeptides Expressed in *Escherichia coli* as Fusions with Glutathione S-Transferase", *Gene*, 67:31-40, 1988.
Solouki et al., "Attomole Biomolecule Mass Analysis by Matrix-Assisted Laser Desorption/Ionization Fourier Transform Ion Cyclotron Resonance", *Anal. Chem.*, 67:4139-4144, 1996.
Sooknanan et al., "A Detection and Amplification System Uniquely Suited for RNA", *Biotechnology*, 13:563-564, 1995.
Studier et al., "Use of T7 RNA Polymerase to Direct Expression of Cloned Genes", *Methods Enzymol.*, 185:60-89, 1990.
Suto et al., "Selection of an Optimal Reporter Gene for Cell-Based High Throughput Screening Assays", *J. Biomol. Screening*, 2(1):7-9, 1997.
Tijssen et al., "Enzyme-linked Immunosorben Assays and Developments in Techniques Using Latex Beads", *Curr. Opin. Immunol.*, 3:233-237, 1991.
van Adrichem et al., "Investigation of Protein Patterns in Mammalian Cells and Culture Supernatants by Matrix-Assisted Laser Desorption/Ionization Mass Spectrometry", *Anal. Chem.*, 70:923-930, 1998.
Van Brunt, J., "Amplifying Genes: PCR and Its Alternatives", *Biotechnology*, 8:291-294, 1990.
Vastzis et al., "Discovery of Three Genes Specifically Expressed in Human Prostate by Expressed Sequence Tag Database Analysis", *Proc. Natl. Acad. Sci. USA*, 95:300-304, 1998.
Ward et al., Binding Activities of a Repertoir of Single Immunoglobulin Variable Domains Secreted from *Escherichia coli*, *Nature*, 341:544-546, 1989.
Watson et al., "Molecular Biology of the Gene", 4th Edition, 1987, The Benjamin/Cummins Pub. Co., p. 224.
Weickert et al., "Turnover of Recombinant Human Hemoglobin in *Escherichia coli* Occurs Rapidly for Insoluble and Slowly for Soluble Globin", *Arch. Biochem. Biophys.*, 348(2):337-346, 1997.
Whittal et al., "Nanoliter Chemistry Combined with Mass Spectrometry for Peptide Mapping of Proteins from Single Mammalian Cell Lysates", *Anal. Chem.*, 70:5344-5347, 1998.
Wilson et al., "Phage Display: Applications, Innovations, and Issues in Phage and Host Biology", *Can. J. Microbiol.*, 44:313-329, 1998.
Woo et al., "The Advance of Technology as a Prelude to the Laboratory of the Twenty-First Century", *Clin. Lab. Med.*, 14:459-471, 1994.
Wu et al., "The Ligation Amplification Reaction (LAR)—Amplification of Specific DNA Sequences Using Sequential Rounds of Template-Dependent Ligation", *Genomics*, 4:560-569, 1989.
Xiang et al., "A Method to Increase Contaminant Tolerance in Protein Matrix-assisted Laser Desorption/Ionization by the Fabrication of Thin Protein-doped Polycrystalline Films", *Rapid Commun. Mass Spectrom.*, 8:199-204, 1994.
US 5,382,513, 01/1995, Lam et al. (withdrawn)

* cited by examiner

MULTIPLEXED PROTEIN EXPRESSION AND ACTIVITY ASSAY

RELATED APPLICATIONS

Benefit of priority under 35 U.S.C. § 119(e) is claimed to U.S. provisional application Ser. No. 60/254,958, filed Dec. 11, 2000, to Joseph A. Monforte, entitled "MULTIPLEXED PROTEIN EXPRESSION AND ACTIVITY ASSAY." The subject matter of the provisional application is incorporated herein in its entirety.

BACKGROUND

The international pharmaceutical market is under increasing pressure to develop new methods for the identification of novel therapeutics and drugs. Most diseases are complex, with multiple genes contributing to susceptibility, initiation, progression and modulation of the disease. Unlike diseases caused by single gene defects, the majority of human diseases are determined by the additive and synergistic interactions between gene products and the environment. Common diseases are, in effect, emergent properties of a complex system. It may not be specific biological elements that are flawed, but a combination of conditions that gives rise to a diseased state. Analyzing these emergent properties and elucidating the network of such interactions can make it possible to identify optimal, valid targets and drugs to treat common diseases.

The central dogma of biology describes the transfer of genetic information from DNA to RNA to protein, with the vast majority of cellular activity being controlled at the protein level. While enormous progress has been made in the areas of DNA and RNA analysis, protein analysis remains labor-intensive and difficult. Protein analysis is further complicated because of the diverse activities and characteristics of proteins. Protein expression levels, catalytic protein activities, protein modifications, protein-protein interactions, protein-nucleic acid interactions, and protein-small molecule interactions combine in a multitude of ways to yield a highly complex network of interactions within cells. Elucidation of the functions of many proteins, and the pathways and networks in which they interact, can lead to the discovery of the overall biological properties of a given system. These properties reveal themselves, or emerge, as one proceeds along the experimental path.

To fully analyze the properties of a complex system, it is generally necessary to perform complex biological experiments, involving thousands of samples (see, e.g., Houston et al. (1997) *Curr. Opin. Biotechnol.* 8:734–40). These experiments involve systematic perturbation of cellular systems and subsequent monitoring of hundreds of variables. Analysis of this information can be used to elucidate the emergent properties of the biological system and lead to a better understanding of the complex pathways involved in diseases. Systems currently available do not monitor the expression levels and functional state of hundreds of proteins within each experiment.

Current technologies for protein expression analysis can be placed into two categories: probing via immunodetection and direct visualization. Immunodetection methods, such as western blots and enzyme-linked immunoabsorbent assays (ELISAs), use antibodies to recognize and bind to a protein and produce a corresponding signal (see, e.g., Gonzalez et al. (1998) *Curr. Opin. Biotechnol.* 9:624–31; Sarubbi et al. (1996) *Anal. Biochem.* 237:70–5; Tijssen et al. (1991) *Curr. Opin. Immunol.* 3:233–237; and Woo et al. (1994) *Clin. Lab. Med.* 14:459–71). ELISA assays use antibodies produced by and harvested from a host that has been inoculated with an antigen, and are typically analyzed individually and occasionally in duplexes. Multiple antibodies can be used to map the physical structure of a protein.

In addition, a number of direct visualization technologies have been used to detect and monitor proteins. Two-dimensional gel systems are used for the large-scale analysis of complex mixtures of proteins. These systems are capable of analyzing up to 10,000 proteins in a single gel (see, e.g., Arnott et al. (1998) *Anal. Biochem.* 258:1–18; and Celis et al. (1999) *Curr. Opin. Biotechnol.* 10:16–21), but are laborious to produce and challenging to analyze.

Another direct analysis method involves the construction of protein/reporter gene conjugates. In this case, the expression of a protein is monitored by detecting a expression of a detectable reporter protein, such as a green fluorescence protein, whose encoding nucleic acid sequence is physically coupled to the gene encoding a protein of interest (see, e.g., Gonzalez et al. (1998) *Curr. Opin. Biotechnol.* 9:624–31; and Suto et al. (1997) *J. Biomol. Screening* 2:7–9). Reporter gene systems have been exploited in high throughput screening systems and provide information about the activity of a particular protein. There are issues related to the impact of the conjugates on gene. These reporter systems generally only allow one or two proteins to be monitored simultaneously and are limited to the cell types into which these constructs can be introduced.

Use of the different protein detection technologies listed above is limited to either measuring a few proteins in a large number of samples or measuring thousands of proteins in small numbers of samples. The need to monitor tens to hundreds of proteins, including their expression levels and functional state, in a high throughput fashion has yet to be fulfilled. Therefore, it is an object herein to fulfill this and other needs.

SUMMARY

Multiplexed assays for determining protein expression levels and activity that provide the above-noted features and many others are provided. The assays provided herein can simultaneously monitor hundreds of proteins within a sample. An exemplary assay employs display binding proteins, such as phage-displayed antibodies, to which proteins of interest bind. Each phage can contain a marker component. After binding to the protein or proteins of interest, the phage or the marker component within the phage, if necessary or desired, is amplified, and the marker component detected, such as with mass spectrometry. The quantity of marker component detected is directly related to the amount of protein in the sample.

Hence, provided are methods of detecting one or more polypeptide in a sample. Exemplary samples include, but are not limited to, proteins, biotinylated proteins, isolated proteins, recombinant proteins, enzymes, enzyme substrates, cancer proteins, or disease related proteins. In some embodiments, the sample contains one or more biomolecules, which can be derived from one or more cell(s). Cells, which include eukaryotic plant and animal cells and prokaryotic cells, can be derived from any suitable source, such as from a tissue sample, a blood sample, a cell lysate and a plurality of cultured cells.

Methods provided herein include the steps of contacting a sample, such as a blood or other body fluid or tissue sample that contains one or more polypeptides of interest, with at least one genetic package, such as a bacteriophage, a baculovirus, or a bacterium. Bacteriophages of interest include, but are not limited to, T4 phage, M13 phage, λ phage and any other phage known to those of skill in the art. The genetic package is selected to display a polypeptide-binding component, such as an antibody on its surface. Other polypeptide-binding components, include, but are not limited to, antibody fragments, single chain antibody fragments, enzymes, biotin, avidin, streptavidin, ligands and receptors. The antibodies, antibody fragments or single chain antibody fragments generally contain one or more antigen recognition regions that bind to a target polypeptide. Contacting the sample with the genetic package includes contacting the sample with a plurality of bio-displayed polypeptide binding components that can bind to one or more target polypeptides in the sample. The plurality of bio-displayed polypeptide binding components can contain about $10^2$ to about $10^{10}$ different polypeptide-binding components. For example, in a screening assay, $10^2$ to about $10^5$ different polypeptide-binding components can be used.

In addition, the genetic package can contain a predetermined marker component for detection. The polypeptide binding component displayed on the genetic package specifically binds to at least one of the one or more target polypeptides in the sample. Each bio-displayed polypeptide-binding component can be associated with a different marker component, resulting in a plurality of marker components. In some embodiments, the plurality of marker components includes a plurality of related marker components, such as, in one exemplary embodiment, a signature polypeptide derived from hemoglobin. In some embodiments, the marker component includes a nucleic acid, which nucleic acid encodes a polypeptide, which polypeptide is expressed on the surface of the genetic package or in a bacterial host upon amplification of the genetic package within the host.

In some embodiments, the genetic package or the one or more target polypeptides in the sample is bound to a solid support, such as a microsphere or bead, the surface of a tube or plate, or a filter membrane. For example, an antibody is optionally used to bind a target polypeptide to the surface of a bead. The solid support can be washed after the polypeptide binding component specifically binds the one or more target polypeptides to remove any unbound components.

In some embodiments, the genetic packages, which bind to target polypeptides via the polypeptide binding component, are then amplified, generally after release from a solid support, resulting in an amplified genetic package. For example, in some embodiments, the marker component includes a nucleic acid, which is expressed in a bacterial host in which the genetic package has been amplified. In other embodiments, the marker component within the genetic package is amplified instead of the genetic package. Amplification methods, include any suitable methods known to those of skill in the art, including, but not limited to, the polymerase chain reaction, the ligase chain reaction, Qβ-replicase amplification and other such amplification methods.

The method further includes detecting the marker component or its expression product in the amplified genetic package or detecting the amplified marker component. The presence of the marker component in the genetic package indicates the presence of the one or more polypeptide in the sample. In addition, the amount of marker component is also optionally detected and provides an indication of the amount of target polypeptide in the sample and/or the expression level of the target polypeptide or other parameter related to the polypeptide to which the genetic package was bound via the polypeptide-binding component.

Detection in the methods herein can concurrently detect a plurality of polypeptides, including, for example, at least about 10 to about $10^9$ polypeptides, about 50 to about 10,000 polypeptides, 3 to about 500 polypeptides and about 3 to about 100 polypeptides. Detection methods include, but are not limited to, mass spectrometry, such as, for example matrix-assisted laser desorption/ionization (MALDI) time-of-flight (TOF) mass spectrometry, NMR spectroscopy, hybridization, microarray detection, electrophoretic detection, surface plasmon resonance, electrochemical detection, fluorescent detection, chemiluminescent detection, colorimetric detection, electrochemiluminescent detection, and any other suitable detection method.

In another aspect, integrated systems for detecting one or more target polypeptides in one or more samples are provided. The systems can include, for example, a plurality of bio-displayed polypeptide binding components and a solid support containing one or more target polypeptides. The polypeptide binding components are designed or selected to bind to one or more of the target polypeptides. In addition, each polypeptide-binding component is associated with a different marker component, generally with a predetermined marker component.

The system further contains an assay module for amplifying or expressing the marker component and a detection module for receiving the marker component or a derivative thereof. The detection module can generate a plurality of data points based upon the amount of each marker component. Detection modules include, but are not limited to, a mass spectrometer, such as, for example, a high throughput mass-spectrometer, an NMR spectrometer, an optical detector, a fluorescent detector and an electrochemical detector. The detection module detects the different marker components and generally determines an amount of each different marker component, which correlates to the amount of various target polypeptides in the sample.

The system further contains an analyzing module in operational communication with the detection system. The analyzing module contains a computer or computer readable medium containing one or more instruction set for correlating the amount of the one or more different marker component with the one or more polypeptide. The analyzing module can be programmed to calculate a ratio of at least a first marker component to at least a second marker component and correlates the ratios to a ratio of at least a first target polypeptide to at least a second target polypeptide in the one or more sample. The computer or computer readable medium contains an instruction set for organizing the data points generated by the detection module into a database, which database contains a profile for one or more sample. The profile for the one or more sample identifies an expression level of at least one target polypeptide in the sample and/or a functional state of at least one target polypeptide in the sample. The instruction set(s) include, for example, software for generating a graphical representation of the amount of the one or more polypeptides, and/or software for performing statistical analysis, such as, but are not limited to, multivariate analysis, principle component analysis and difference analysis, for the plurality of data points. In addition, the system further contains an output file embodied in a computer readable medium.

During operation of the system, the assay module is can be operably coupled to the solid support and the detection system. In addition, the mass spectrometer can be operably coupled to the solid support and to the assay system.

DETAILED DESCRIPTION

A. Definitions

Figure 1:
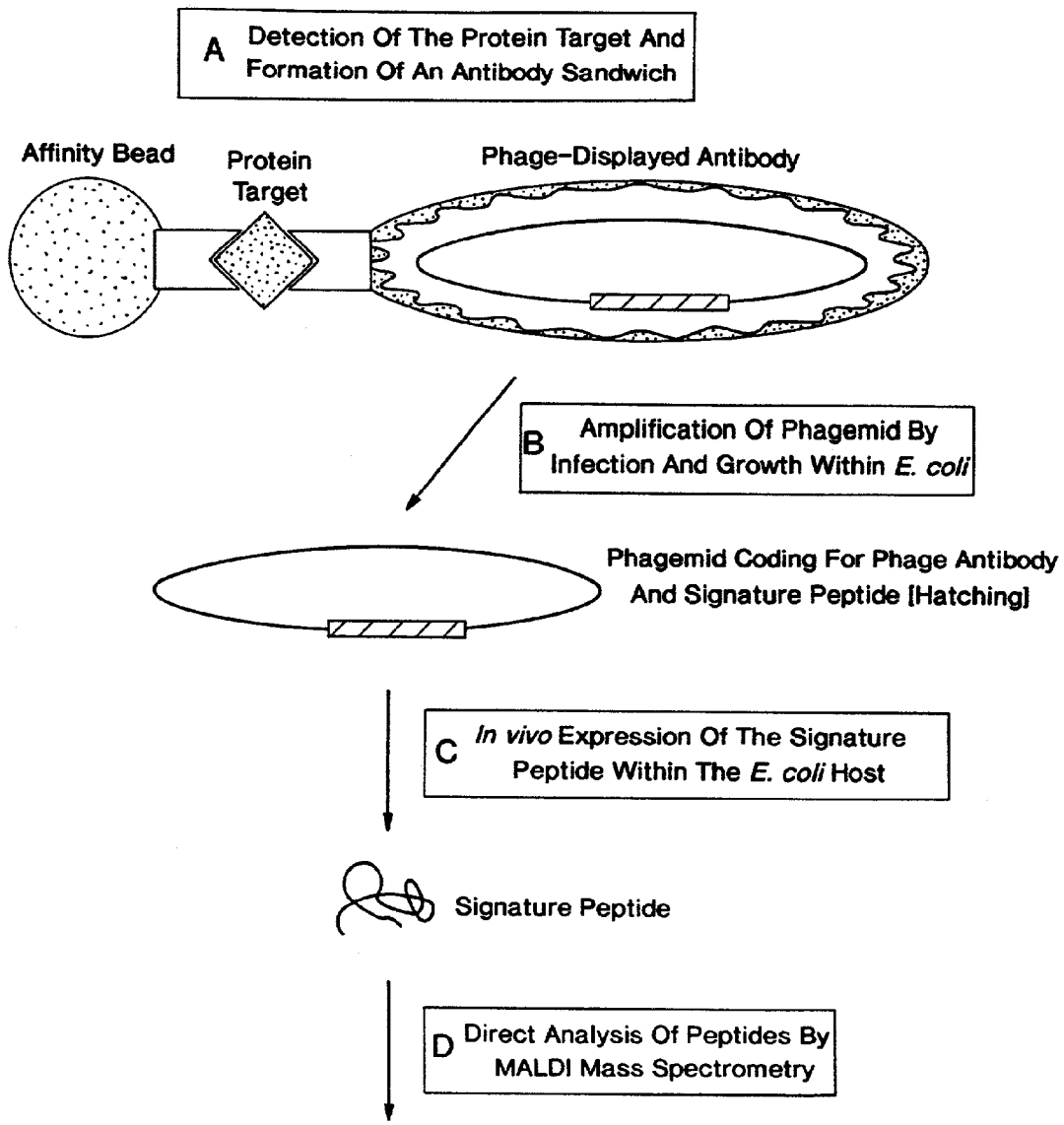
FIG. 1 provides a schematic overview of an exemplary embodiment: in step A, a target protein attached to an affinity bead is recognized by a phage-displayed antibody, thus forming an antibody sandwich. Step B illustrates infection of a host cells, such as E. coli, with the phage, each of which contains a unique marker. The phage are then amplified exponentially within the bacterial host. As depicted in the example in the FIGURE, the unique marker component contains signature polypeptide, which is then expressed within the bacterial host, as illustrated by step C. In step D, a sample of bacteria is spotted onto a mass spectrometric plate and the signature polypeptide is detected and quantitated.

Unless defined otherwise, all technical and scientific terms used herein have the same meaning as is commonly understood by one of skill in the art to which this invention belongs. All patents, patent applications, published applications and publications referred to throughout the disclosure herein are, unless noted otherwise, incorporated by reference in their entirety. In the event that there are a plurality of definitions for terms herein, those in this section prevail.

As used herein, high-throughput screening (HTS) refers to processes that test a large number of samples, such as samples of test proteins or cells containing nucleic acids encoding the proteins of interest to identify structures of interest or to identify test compounds that interact with the variant proteins or cells containing them. HTS operations are amenable to automation and can be computerized to handle sample preparation, assay procedures and the subsequent processing of large volumes of data.

As used herein, signal refers to any detectable output, such as that generated by a reporter gene or by a mass spectrometer.

As used herein, "reporter" or "reporter moiety" refers to any moiety that allows for the detection of a molecule of interest, such as a protein expressed by a cell. Reporter moieties include, include, for example, fluorescent proteins, such as red, blue and green fluorescent proteins (see, e.g., U.S. Pat. No. 6,232,107, which provides GFPs from Renilla species and other species), the lacZ gene from E. coli and other such well-known genes that encode detectable products.

As used herein, monitoring a protein refers to the detection or measurement of the protein, including, but are not limited to, its, the expression level and functional state.

As used herein, molecules derived from one or more cells are "biomolecules."

As used herein, NMR refers to nuclear magnetic resonance. An NMR experiment is based on the resonant absorption of radio frequency (rf) radiation by nuclei exposed to a magnetic field. "Nuclei," as used herein, refers to atomic nuclei. Many atomic nuclei possess spin angular momentum. A nucleus with a spin quantum number (I) has angular momentum and a magnetic moment. For example, I=½ for a proton. To be detectable by NMR a nucleus must have a non-zero spin. NMR-detectable nuclei include, but are not limited to, $^1H$, $^{13}C$, $^{19}F$, $^{31}P$, and $^{15}N$. The term, "NMR detectable chemical shift," refers to a signal due to the absorption of rf radiation by one or more NMR-detectable nuclei. The signal leads to an NMR spectrum, which is a plot of absorption of rf radiation against chemical shift (*).

As used herein, a sample refers to any composition or mixture that contains a target polypeptide. Samples may be derived from biological or other sources. Biological sources include eukaryotic and prokaryotic sources, such as plant and animal cells, tissues and organs.

As used herein, target polypeptides or proteins are polypeptides or proteins of interest and include, but are not limited to, for example, cancer proteins and other disease related proteins.

As used herein, polypeptide binding components are any components or moieties that are used to bind to and/or recognize a target polypeptide. Genetic packages, such as bacteriophage and bacteria, can be used display a plurality of polypeptide-binding components.

As used herein, polypeptides of interest are referred to herein as "target polypeptides" or "target proteins," which are the proteins assayed for expression levels, such as by detection of an amount or relative amount of protein produced by a cell and/or activity using the methods provided herein.

As used herein, terms "polypeptide," "peptide," and "protein" are used interchangeably herein to refer to a polymer of amino acids linked through peptide bonds. Polypeptides of the include, but are not limited to, proteins, biotinylated proteins, isolated proteins, recombinant proteins, enzymes, enzyme substrates, cancer proteins, or other disease related proteins. In addition, the polypeptides or proteins optionally include naturally occurring amino acids as well as amino acid analogs and/or mimetics of naturally occurring amino acids that function in a manner similar to naturally occurring amino acids. A sample can contain multiple target proteins.

As used herein, a biotinylated protein is a protein linked to biotin to create a detectable complex, through streptavidin or avidin binding. Such binding is used to immobilize a protein and/or render it detectable such as by optional conjugated to an enzyme capable of an enzymatic or chemiluminescent substrate turnover reaction. The reaction is then used to detect the biotinylated polypeptide.

As used herein, a protein or other component is "isolated" when it is partially or completely separated from components with which it is normally associated, such as, for example, other proteins, nucleic acids, cells, synthetic reagents, and the like. A nucleic acid, polypeptide, protein, or the like, is "recombinant" when it is artificial or engineered, or derived from an artificial or engineered protein or nucleic acid.

As used herein, a "cancer protein," refers to any protein, onco-protein, or polypeptide that is involved or believed to be involved in cancer diagnosis, cancer therapy, a cause of cancer, a cure of cancer, or other related aspect.

As used herein, "disease-related proteins" refer to any polypeptides that are involved in or believed to be involved in diagnosis of a disease, the cause of a disease, disease therapy, cure of a disease or other disease aspect or etiology.

As used herein, "genetic package," refers to a biological composition that contains genetic material and that is capable of displaying or exhibiting a polypeptide binding component, such as a polypeptide on its surface. Bacteriophage and baculovirus are exemplary genetic packages.

As used herein, a "bacteriophage" is a bacterial virus or phage containing nucleic acid, a protein coat and sometimes a lipid. The bacteriophage are used as genetic packages and/or bio-display components. For example, a polypeptide binding component or an antibody is expressed on the surface or coat of the bacteriophage, making it available to bind target polypeptides in the samples.

As used herein, "baculovirus" refers to a DNA virus, such as *Autographa california* nuclear polyhedrosis virus (NPV), that infects insect cells. These viruses can be used in the methods herein to display a binding component on their outer surface where it is available to bind to a target polypeptide, such as a polypeptide in a sample.

As used herein, a "bacterium" is a prokaryotic single-celled microorganism that is optionally used to display a polypeptide-binding component on its surface for binding the target polypeptides in the samples.

As used herein, a "bio-displayed component" is a molecule, such as, for example, a polypeptide, such as an antibody, that is displayed for binding on a biological molecule or genetic package, such as a phage. For example, in a phage-displayed antibody, the antibody is the bio-displayed component and the phage is the biological molecule, bio-display component, or genetic package.

As used herein, a "polypeptide binding component" is one that binds, in a specific manner, to a target polypeptide.

As used herein, "specifically binds" to a polypeptide, protein, or other component refers to a binding reaction that is determinative of the presence, e.g., of a target polypeptide in a heterogeneous population of polypeptides and other biologics. Thus when a protein-binding component specific to a target polypeptide binds to that target polypeptide, it binds to that particular target polypeptide preferentially out of a complex mixture. For example, it can bind at least two times the background, generally 10 to 100 times background, and does not substantially bind in significant amounts to other proteins or components in the sample. For example, specific binding to a polyclonal antibody may require an antibody that is selected for its specificity for a particular target protein or target polypeptide as discussed below.

As used herein, "predetermined marker component" is optionally a peptide, a nucleotide, a polypeptide, a polynucleotide, or the like. The predetermined marker components generally have no sequence relation to the target polypeptide to be detected.

As used herein, an "antibody" refers to a polypeptide or protein substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. An exemplary immunoglobulin or antibody structural unit includes a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into an Fab' monomer. The Fab' monomer is essentially Fab with part of the hinge region (see, e.g., *Fundamental Immunology*, W. E. Paul, ed., Raven Press, N.Y. Fourth Edition (1998), for other antibody fragments known to those of skill in the art). While various antibody fragments are defined in terms of the digestion of an intact antibody, one of skill in the art will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Antibodies also include single chain antibodies, including single chain Fv (scFv) antibodies in which a variable heavy and a variable light chain are joined together directly or through a linker, such as a peptide linker, to form a continuous polypeptide. The antibodies, antibody fragments and single chain antibodies include, for example, an antigen recognition region, or a site that specifically recognizes and complexes with a specific antigen or target polypeptide.

For the sake of simplicity, the term "antibody" is used herein to represent any types of affinity proteins that are displayed in the context of a genetic package, such as a bacteriophage.

As used herein, nucleic acids include DNA, RNA and analogs thereof, including protein nucleic acids (PNA) and mixture thereof. Nucleic acids can be single or double stranded. When referring to probes or primers, optionally labeled, with a detectable label, such as a fluorescent or radiolabel, single-stranded molecules are contemplated. Such molecules are generally of a length such that they are statistically unique of low copy number, generally less than 5 or 3, for probing or priming a library. Generally a probe or primer contains at least 14, 16 or 30 contiguous of sequence complementary to or identical a gene of interest. Probes and primers can be 10, 14, 16, 20, 30, 50, 100 or more nucleic acid bases long.

As used herein, a "polynucleotide" or "nucleic acid" of refers to deoxyribonucleotides or ribonucleotides and polymers thereof in either single or double stranded form. The terms include polynucleotides containing nucleotide analogs or modified backbone residues or linkages, including synthetic, naturally occurring, and non-naturally occurring components.

As used herein, mapping the physical structure of a protein refers to process that protein folding or the presence of modifications and changes in a protein structure. Multiple antibodies can be used to map the physical structure of a protein and detect changes in protein folding or the presence of modifications. Epitope mapping can be used to monitor the functional state of a protein.

As used herein, a marker refers to a signature polynucleotide, polypeptide or other moiety that can be directly detected.

As used herein, the amino acids, which occur in the various amino acid sequences appearing herein, are identified according to their known, three-letter or one-letter abbreviations (see, Table 1). The nucleotides, which occur in the various nucleic acid fragments, are designated with the standard single-letter designations used routinely in the art.

As used herein, amino acid residue refers to an amino acid formed upon chemical digestion (hydrolysis) of a polypeptide at its peptide linkages. The amino acid residues described herein are presumed to be in the "L" isomeric form. Residues in the "D" isomeric form, which are so-designated, can be substituted for any L-amino acid residue, as long as the desired functional property is retained by the polypeptide; such residues . $NH_2$ refers to the free amino group present at the amino terminus of a polypeptide.

COOH refers to the free carboxy group present at the carboxyl terminus of a polypeptide. In keeping with standard polypeptide nomenclature described in *J. Biol. Chem.*, 243:3552–59 (1969) and adopted at 37 C.F.R. § § 1.821–1.822, abbreviations for amino acid residues are shown in the following Table:

TABLE 1

Table of Correspondence

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |

It should be noted that all amino acid residue sequences represented herein by formulae have a left to right orientation in the conventional direction of amino-terminus to carboxyl-terminus. In addition, the phrase "amino acid residue" is broadly defined to include the amino acids listed in the Table of Correspondence and modified and unusual amino acids, such as those referred to in 37 C.F.R. § § 1.821–1.822, and incorporated herein by reference. Furthermore, it should be noted that a dash at the beginning or end of an amino acid residue sequence indicates a peptide bond to a further sequence of one or more amino acid residues or to an amino-terminal group such as $NH_2$ or to a carboxyl-terminal group such as COOH.

In a peptide or protein, suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene*, 4th Edition, 1987, The Benjamin/Cummings Pub. co., p. 224).

Such substitutions can be made in accordance with those set forth in TABLE 2 as follows:

TABLE 2

| Original residue | Conservative substitution |
|---|---|
| Ala (A) | Gly; Ser |
| Arg (R) | Lys |
| Asn (N) | Gln; His |
| Cys (C) | Ser |
| Gln (Q) | Asn |

TABLE 2-continued

| Original residue | Conservative substitution |
|---|---|
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions are also permissible and may be determined empirically or in accord with known conservative substitutions.

As used herein, to hybridize under conditions of a specified stringency is used to describe the stability of hybrids formed between two single-stranded DNA fragments and refers to the conditions of ionic strength and temperature at which such hybrids are washed, following annealing under conditions of stringency less than or equal to that of the washing step. Typically high, medium and low stringency encompass the following conditions or equivalent conditions thereto:

1) high stringency: 0.1×SSPE or SSC, 0.1% SDS, 65° C.

2) medium stringency: 0. 2×SSPE or SSC, 0.1% SDS, 50° C.

3) low stringency: 1.0×SSPE or SSC, 0.1% SDS, 50° C.

Equivalent conditions refer to conditions that select for substantially the same percentage of mismatch in the resulting hybrids. Additions of ingredients, such as formamide, Ficoll, and Denhardt's solution affect parameters such as the temperature under which the hybridization should be conducted and the rate of the reaction. Thus, hybridization in 5×SSC, in 20% formamide at 42° C. is substantially the same as the conditions recited above hybridization under conditions of low stringency. The recipes for SSPE, SSC and Denhardt's and the preparation of deionized formamide are described, for example, in Sambrook et al. (1989) *Molecular Cloning, A Laboratory Manual*, Cold Spring Harbor Laboratory Press, Chapter 8; see, Sambrook et al., vol. 3, p. B.13, see, also, numerous catalogs that describe commonly used laboratory solutions). It is understood that equivalent stringencies may be achieved using alternative buffers, salts and temperatures.

As used herein, heterologous or foreign nucleic acid, such as DNA and RNA, are used interchangeably and refer to DNA or RNA that does not occur naturally as part of the genome in which it is present or which is found in a location or locations in the genome that differ from that in which it occurs in nature. Heterologous nucleic acid is generally not endogenous to the cell into which it is introduced, but has been obtained from another cell or prepared synthetically. Generally, although not necessarily, such nucleic acid encodes RNA and proteins that are not normally produced by the cell in which it is expressed. Any DNA or RNA that one of skill in the art would recognize or consider as heterologous or foreign to the cell in which it is expressed is herein encompassed by heterologous DNA. Heterologous DNA and RNA may also encode RNA or proteins that mediate or alter expression of endogenous DNA by affecting transcription, translation, or other regulatable biochemical processes. Examples of heterologous nucleic acid include, but are not limited to, nucleic acid that encodes traceable marker proteins, such as a protein that confers drug resistance, nucleic acid that encodes therapeutically effective substances, such as anti-cancer agents, enzymes and hormones, and DNA that encodes other types of proteins, such as antibodies.

Hence, herein heterologous DNA or foreign DNA, includes a DNA molecule not present in the exact orientation and position as the counterpart DNA molecule found in the genome. It may also refer to a DNA molecule from another organism or species (i.e., exogenous).

As used herein, isolated with reference to a nucleic acid molecule or polypeptide or other biomolecule means that the nucleic acid or polypeptide has separated from the genetic environment from which the polypeptide or nucleic acid were obtained. It may also mean altered from the natural state. For example, a polynucleotide or a polypeptide naturally present in a living animal is not "isolated," but the same polynucleotide or polypeptide separated from the coexisting materials of its natural state is "isolated", as the term is employed herein. Thus, a polypeptide or polynucleotide produced and/or contained within a recombinant host cell is considered isolated. Also intended as an "isolated polypeptide" or an "isolated polynucleotide" are polypeptides or polynucleotides that have been purified, partially or substantially, from a recombinant host cell or from a native source. For example, a recombinantly produced version of a compounds can be substantially purified by the one-step method described in Smith and Johnson, Gene 67:31–40 (1988). The terms isolated and purified are sometimes used interchangeably.

As used herein, receptor refers to a biologically active molecule that specifically binds to (or with) other molecules. The term "receptor protein" may be used to more specifically indicate the proteinaceous nature of a specific receptor.

As used herein, a promoter region refers to the portion of DNA of a gene that controls transcription of the DNA to which it is operatively linked. The promoter region includes specific sequences of DNA that are sufficient for RNA polymerase recognition, binding and transcription initiation. This portion of the promoter region is referred to as the promoter. In addition, the promoter region includes sequences that modulate this recognition, binding and transcription initiation activity of the RNA polymerase. These sequences may be cis acting or may be responsive to trans acting factors. Promoters, depending upon the nature of the regulation, may be constitutive or regulated.

As used herein, the phrase "operatively linked" generally means the sequences or segments have been covalently joined into one piece of DNA, whether in single or double stranded form, whereby control or regulatory sequences on one segment control or permit expression or replication or other such control of other segments. The two segments are not necessarily contiguous. For gene expression a DNA sequence and a regulatory sequence(s) are connected in such a way to control or permit gene expression when the appropriate molecular regulators, such as transcriptional activator proteins, are bound to the regulatory sequence(s).

As used herein, a composition refers to any mixture of two or more products or compounds. It may be a solution, a suspension, liquid, powder, a paste, aqueous, non-aqueous or any combination thereof.

As used herein, a combination refers to any association between two or more items. A combination can be packaged as a kit.

As used herein, "packaging material" refers to a physical structure housing the components (e.g., one or more regulatory regions, reporter constructs containing the regulatory regions or cells into which the reporter constructs have been introduced) of the kit. The packaging material can maintain the components sterilely, and can be made of material commonly used for such purposes (e.g., paper, corrugated fiber, glass, plastic, foil, ampules, etc.). The label or packaging insert can include appropriate written instructions, for example, practicing a method provided herein.

As used herein, substantially identical to a product means sufficiently similar so that the property of interest is sufficiently unchanged so that the substantially identical product can be used in place of the product.

As used herein, the term "vector" refers to a nucleic acid molecule capable of transporting another nucleic acid to which it has been linked. One type of vector is an episome, i.e., a nucleic acid capable of extra-chromosomal replication. Other exemplary vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. "Plasmid" and "vector" are used interchangeably as the plasmid is the most commonly used form of vector. Other such other forms of expression vectors that serve equivalent functions and that become known in the art subsequently hereto.

As used herein, an array refers to a collection of elements, such as nucleic acid molecules or polypeptides, containing three or more member elements; arrays can be in solid phase or liquid phase. An addressable array or collection is one in which each member of the collection is identifiable typically by position on a solid phase support or by virtue of an identifiable or detectable label, such as by color, fluorescence, electronic signal (i.e. RF, microwave or other frequency that does not substantially alter the interaction of the molecules of interest), bar code or other symbology, chemical or other such label. Hence, in general the members of the array are immobilized to discrete identifiable loci on the surface of a solid phase or directly or indirectly linked to or otherwise associated with the identifiable label, such as affixed to a microsphere or other particulate support (herein referred to as beads) and suspended in solution or spread out on a surface. The collection can be in the liquid phase if other discrete identifiers, such as chemical, electronic, colored, fluorescent or other tags are included.

As used herein, a substrate (also referred to as a matrix support, a matrix, an insoluble support, a support or a solid support) refers to any solid or semisolid or insoluble support to which a molecule of interest, such as a biological molecule, organic molecule or biospecific ligand is linked or contacted. Such materials include any materials that are used as affinity matrices or supports for chemical and biological molecule syntheses and analyses, such as, but are not limited to: polystyrene, polycarbonate, polypropylene, nylon, glass, dextran, chitin, sand, pumice, agarose, polysaccharides, dendrimers, buckyballs, polyacrylamide, silicon, rubber, and other materials used as supports for solid phase syntheses, affinity separations and purifications, hybridization reactions, immunoassays and other such applications. The support herein may be particulate or may be a be in the form of a continuous surface, such as a microtiter dish or well, a glass slide, a silicon chip, a nitrocellulose sheet, nylon mesh, or other such materials. When particulate, typically the particles have at least one dimension in the 5–10 mm range or smaller. Such particles, referred collectively herein as "beads", are often, but not necessarily, spherical. Such reference, however, does not constrain the geometry of the matrix, which may be any shape, including random shapes, needles, fibers, and elongated. Roughly spherical "beads", particularly microspheres that can be used in the liquid phase, are also contemplated. The "beads" may include additional components, such as magnetic or paramagnetic particles (see, e.g., Dyna beads (Dynal, Oslo, Norway)) for separation using magnets, as long as the additional components do not interfere with the methods and analyses herein.

As used herein, matrix or support particles or beads refers to support materials that are in the form of discrete particles. The particles have any shape and dimensions, but typically have at least one dimension that is 100 mm or less, 50 mm or less, 10 mm or less, 1 mm or less, 100 µm or less, 50 µm or less and typically have a size that is 100 mm$^3$ or less, 50 mm$^3$ or less, 10 mm$^3$ or less, and 1 mm$^3$ or less, 100 µm$^3$ or less and may be on order of cubic microns. Such particles are collectively called "beads."

As used herein, the database means a collection of information, such as two or more regulatory region sequences. Databases are generally are stored on computer readable medium so that they may be accessed and analyzed.

As used herein, the singular forms "a", "and," and "the" include plural referents unless the context clearly indicates otherwise. Thus, for example, reference to "a gene regulatory region" includes a plurality of such regulatory regions and reference to "a cell" includes reference to one or more such cells.

As used herein, "concurrently" and "simultaneously" refer to two events, such as binding or detection events, that occur at essentially the same time. For example, two or more signature polypeptides in a sample are detected concurrently in a mass spectrometer. A sample generally contains about 1 to about 100 or 1000 or more different marker components.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942–944).

B. Assays

Multiplexed assays for protein expression and activity are provided. Such assays can be used to understand the function of complex systems that include a multitude of proteins and to understand the pathways and networks in which such proteins interact. Provided are assays for monitoring such complex systems by simultaneously monitoring the expression level and/or functional states of target proteins. Hundreds and thousands of proteins can be monitored simultaneously.

The assays simultaneously monitor the expression levels and functional state of a plurality of target proteins. The protein detection begins in a manner similar to a classic two-antibody sandwich assay. One binding moiety, such as an antibody, is attached to a solid phase support, such as synthetic microspheres or "beads" or flat support, and captures a target protein. A second binding moiety, such as a second antibody, recognizes the captured target protein and binds to it, forming the two-binding moiety-target protein sandwich. Attached to the second binding moiety is a signal-generating element. In a standard ELISA, this element might be an enzyme, such as horse radish peroxidase (HRP). In the methods provided herein, the signal-generating element is a genetic package, such as a bacteriophage, that can infect and multiply within a host (the amplification component) and also code for the expression of a unique signature polypeptide (the detectable signal component) that is subsequently detected. In embodiments herein the signature polypeptide is detected and quantitated by mass spectrometry.

There are a number of advantages to this signal-generating scheme over a standard ELISA. These include a high level of multiplexing, since tens to hundreds of simultaneous detection events can be performed, and exponential amplification, which provides a high level of sensitivity. The assay methods incorporate these advantages while adding very little complexity to the overall assay process.

In one embodiment, a polypeptide binding component is displayed on a genetic package, such as a phage displayed antibody or binding portion thereof, and used to bind the target proteins. The genetic package contains a predetermined marker component, such as a signature polypeptide or polynucleotide, that is detected and correlated to the amount of target protein bound by the polypeptide binding component on the genetic package.

The phage or other genetic marker contains a marker component, such as nucleic acid encoding a signature polypeptide. After binding to the target protein or target proteins of interest, the phage or the marker component within the phage can be amplified and the marker component detected. Detection can be effected by any suitable method, such as mass spectrometry. The quantity of marker component detected directly correlates with the amount of target protein in the sample.

Thus provided are assays that analyze several target polypeptides or proteins in a single assay. Because most diseases are complex, i.e., involving multiple genes that contribute to susceptibility, initiation, progression, and modulation of the disease, such as cancer, the present assays are particularly useful for analyzing additive and synergistic interactions between gene products to produce a better understanding of diseases. By analyzing all proteins involved in a disease, such as the entire cell contents of a diseased cell, the present assays identify emergent properties of the complex systems and lead to elucidation of the network of interactions involved in the disease, thus leading to identification of optimal, valid targets and drugs to treat such diseases.

For example, in one embodiment, phage-displayed antibodies are used to simultaneously detect relative expression levels and physical attributes of tens to hundreds of proteins in a sample. The phage-displayed antibodies contain a direct linkage between the binding moiety, i.e., the antibody, and DNA coding sequences, which are encode a signature component, such as a polypeptide or a polynucleotide. This feature, combined with the infection and growth capabilities of phage, provides a multiplexed assay system that expresses and can amplify the signature component, which is then detected and correlated to the target polypeptides in the sample that bound to the phage-displayed antibodies.

1. Components of the Methods a. Samples

As noted, a sample generally contains one or more biomolecules. Samples can be from any source including biological materials, such as body fluids, tissues and organs, cells from prokaryotic or eukaryotic organisms. The cells can be plant or animal cells. Thus, cells include any cells known to those of skill in the art and include, but are not limited to, cells derived from a sample, such as a tissue sample, a body fluid, including blood, sweat, urine, synovial fluid and cerebral spinal fluid (CSF) samples, a tissue or organ sample, a cell lysate, or a sample from plurality of cultured cells. Such samples generally contain and/or express polypeptides and/or proteins of interest. Alternatively, the samples are mixtures, such as isolated or recombinant polypeptides for which an assay is desired, such as to determine functional state. A sample can contain about 3 to about 100 or about 500 target polypeptides or about 50 to about 10,000 target polypeptides or about 100 to 5000 target polypeptides or more up to any desired number, including, for example, all proteins in a cell or tissue or cell culture lysate. In some embodiments, the target polypeptides contain biotin, avidin, lectin, a small organic molecule or other moiety to aid in isolation, immobilization and/or detection.

The methods and integrated systems provided herein optionally are used to analyze any target polypeptide or mixture of target polypeptides. The target polypeptides are generally in a sample, which is assayed using genetic packages displaying polypeptide binding components as described herein. The target proteins bind to the bio-display binding moieties, such as bio-displayed polypeptides, such as antibodies or fragments thereof.

Each bio-displayed polypeptide binding component is associated with a predetermined marker, which is used as a signal component to detect the target polypeptide. The samples are contacted with the bio-displayed components for binding to occur. For example, the target polypeptides of the sample are bound to a solid support, and the bio-displayed polypeptide binding components are applied to the solid support. After removal of any unbound polypeptide binding component, the genetic package or bio-display component is amplified, or the predetermined marker component within the genetic package is amplified, and the marker components are detected and optionally quantitated. The presence of and amount of each marker component correlates to the presence of and amount of the target polypeptide to which the genetic package associated with the marker component was bound, such as, for example, via a polypeptide binding component. Each of these steps and components is described in more detail below.

b. Bio-Displayed Components

The methods provided herein use a plurality of bio-displayed components that specifically bind to target proteins. The bio-displayed components are polypeptide binding components displayed on a genetic package. Protein detection of target proteins generally employs a binding assay similar to a classic two-antibody sandwich assay. In the classic antibody sandwich, one antibody is attached to a solid support and captures the target protein. A second antibody recognizes the captured target protein and binds to it, forming the two-antibody sandwich. In the classic experiment, a signal-generating element or label is attached to the second antibody and is used to detect the target proteins. In the methods herein, the signal is generated by the displaying genetic package, which encodes a signal molecule that identifies or is associated with the displayed molecule. A genetic package containing a predetermined marker component as the signal-generating element is used in the methods herein. The signal molecule is generally a polypeptide, designated a signature polypeptide, which is then detected, such as by mass spectrometry.

An exemplary embodiment is illustrated in FIG. 1. A first polypeptide binding component is captured on a surface as shown in step A. The surface is contacted with a sample and the target polypeptides bind to the first polypeptide binding component. The target polypeptide is then contacted with a second polypeptide-binding component by contacting the captured target polypeptides with a plurality of bio-displayed polypeptide binding components, such as, for example, an antibody or portion thereof displayed on a genetic package, such as a bacteriophage. Each member of the plurality of bio-displayed polypeptide components is associated with a predetermined marker component that is encoded by the genetic package and, which is used, after optional amplification, and expression within a bacterial host as in steps B and C, to detect the bound target polypeptides. The predetermined marker contains a unique signature polypeptide or nucleic acid that is amplified, detected (the signal-generating element), and quantitated as illustrated in step D. The amount of each predetermined marker component detected corresponds to the amount or relative amount of each target polypeptide.

This signal-generating scheme has a number of advantages over the classical two-body antibody sandwich assay, such as that used with ELISA. For example, a high level of multiplexing is optionally achieved. Tens of hundreds of binding events can be simultaneously detected. In addition, exponential amplification of the marker component provides a high level of sensitivity. For example, target proteins A, B, and C, are expressed at the relative ratios of 10, 3, and 1, respectively. Target proteins A, B, and C are captured on the solid surface of FIG. 1 and form two-antibody sandwiches with, e.g., phage displayed antibodies in the stoichiometric ratios of 10, 3, and 1. Following a wash step to remove unbound components, the different bound bacteriophages (A, B, and C) are eluted and used to infect a plurality of host cells, such as a bacterial host, including, but are not limited to, *E. coli*. A single phage is capable of infecting a single host cell; the classes of infected hosts are proportional to the relative ratios of the different classes of eluted phage. The host cells grow exponentially in polyclonal fashion, thus maintaining the 10-3-1 ratio of the infecting phage. The ratios are then reflected in the levels of different signal polypeptides expressed by the polyclonal host cells. As a result, each of 10 host cells express a signature polypeptide correlating to target protein A; each of 3 hosts express a signature polypeptide associated with target protein B, and 1 host expresses a signature polypeptide correlating to target protein C. The aggregate expression of the different target proteins is then detected by any suitable means, such as by mass spectrometry. The relative signal level for the signature polypeptides detected is 10, 3, and 1. The eluting, mixing, incubating, and detection, such as, for example, by spotting on a mass spectrometer plate, are all optionally performed using only two pipetting steps, making the entire procedure only slightly more complicated than a standard ELISA, while it provides significantly more information than an ELISA assay. The simplicity of the assay allows for a high degree of multiplexing.

c. Genetic Packages

Genetic packages refer to any replicable vector, such as a phage, virus or bacterium, that can display a protein binding-moiety. The plurality of bio-displayed polypeptide binding components is displayed by a genetic package in such a way as to allow the polypeptide binding component, such as a ligand or receptor, to bind to a target polypeptide. Exemplary genetic packages include, but are not limited to, bacteriophages (see, e.g., Clackson et al. (1991) Making Antibody Fragments Using Phage Display Libraries, *Nature*, 352:624–628; Glaser et al. (1992) Antibody Engineering by Condon-Based Mutagenesis in a Filamentous Phage Vector System, *J. Immunol.*, 149:3903–3913; Hoogenboom et al. (1991) Multi-Subunit Proteins on the Surface of Filamentous Phage: Methodologies for Displaying Antibody (Fab) Heavy and Light Chains, *Nucleic Acids Res.,* 19:4133–41370), baculoviruses (see, e.g., Boublik et al. (1995) Eukaryotic Virus Display: Engineering the Major Surface Glycoproteins of the *Autographa* California Nuclear Polyhedrosis Virus (ACNPV) for the Presentation of Foreign Proteins on the Virus Surface, *Bio/Technology,* 13:1079–1084), bacteria and other suitable vectors for displaying a protein, such as a phage-displayed antibody. For example bacteriophages of interest include, but are not limited to, T4 phage, M13 phage and λ phage. Genetic packages are optionally amplified such as in a bacterial host. Alternatively or in addition, a predetermined marker component within the genetic package is expressed and/or amplified. Any of these genetic packages as well as any others known to those of skill in the art, are used in the methods provided herein to display a polypeptide binding component, i.e., to serve as a bio-display component.

d. Polypeptide Binding Components

Bio-displayed components are used to bind to target polypeptides in a sample. Such bio-displayed components can be polypeptide binding components. The "polypeptide-binding moiety" can be a bio-displayed polypeptide binding component that binds to a target polypeptide in a sample. Exemplary polypeptide binding components include, but are not limited to, antibodies, antibody fragments, single chain antibodies, antigen recognition regions, enzymes, biotin, avidin, streptavidin, ligands, receptors, other polypeptides, carbohydrates, lipids, nucleic acids, and the like. The target polypeptide to which the bio-displayed component binds is detected by correlating the binding event to a predetermined marker in the genetic package which displays the polypeptide binding component on its surface.

In one embodiment, the "polypeptide binding component," includes an antibody or binding portion thereof. Antibodies include, monoclonal and polyclonal antibodies and antisera that specifically bind to an antigen, such as a target polypeptide, with a binding constant KD of at least about 0.1 µM, generally at least about 0.01 µM or better, and generally and 0.001 µM or better.

For preparation of monoclonal or polyclonal antibodies, any technique known in the art can be employed. Such methods are well known (see, e.g., Coligan et al. (eds.) (1991) *Current Protocols in Immunology* Wiley & Sons, NY; Harlow et al. (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; Goding (1996) *Monoclonal Antibodies: Principles and Practice* (3rd ed.) Academic Press, New York, N.Y.; and Kohler et al. (1975) *Nature* 256:495–497). Other suitable techniques for antibody preparation include selection of libraries of recombinant antibodies in phage or similar vectors(see, e.g., Huse et al. (1989) *Science* 246:1275–1281; and Ward et al.(1989) *Nature* 341:544–546).

In another embodiment, the polypeptide binding component includes a ligand or a receptor. A ligand binds specifically to a particular receptor, anti-ligand, or target molecule, such as a target polypeptide. Any ligand that specifically binds a target polypeptide is optionally used as a polypeptide binding component and displayed on a genetic package as described herein. The polypeptide binding component and the target polypeptide optionally form a specifically bound ligand/receptor complex when the ligand is contacted with the receptor displayed on the surface of a genetic package such as a phage. The ligand/receptor complex is then used to identify the target polypeptide as described herein.

e. Phage-Displayed Antibodies

1) Phage, Viruses and Bacteria for Displaying Binding Polypeptides

Phage, viruses, bacteria and other such manipulable hosts and vectors (referred to as biological particles) can be modified to express selected antigens (peptides or polypeptides) on their surfaces by, for example, inserting DNA encoding the antigen into the host or vector genome, at a site such as in the DNA encoding the coat protein, such that upon expression the antigen (peptide or polypeptide) is presented on the surface of the virus, phage or bacterial host. Libraries of such particles that express diverse or families of proteins on their surfaces can be prepared and the resulting library is screened with target proteins (i.e. receptors or ligands). Those viruses with the highest affinity for the targeted antigen (receptor or ligand) can be selected (see, e.g., U.S. Pat. Nos. 5,403,484, 5,395,750, 5,382,513, 5,316,922, 5,288,622, 5,223,409, 5,223,408 and 5,348,867).

Libraries can be prepared that contain modified binding sites or synthetic antibodies. DNA molecules, each encoding proteins containing a family of similar potential binding domains and a structural signal calling for the display of the protein on the outer surface of a selected viral or bacterial or other package, such as a bacterial cell, bacterial spore, phage, or virus are introduced into the bacterial host, virus or phage. The protein is expressed and the potential binding domain is displayed on the outer surface of the particle. The cells or viruses bearing the binding domains to which target molecules bind are isolated and amplified, and then are characterized. In one embodiment, one or more of these successful binding domains is used as a model for the design of a new family of potential binding domains, and the process is repeated until a novel binding domain having a desired affinity for the target molecule is obtained. For example, libraries of de novo synthesized antibody fragments expressed on the surface have been prepared. DNA encoding synthetic antibodies, which have the structure of antibodies, specifically Fab or Fv fragments, and contain randomized binding sequences that may correspond in length to hypervariable regions (CDRs) can be inserted into such vectors and screened with an antigen of choice.

Synthetic binding site libraries can be manipulated and modified for use in combinatorial type approaches in which the heavy and light chain variable regions are shuffled and exchanged between synthetic antibodies in order to affect specificities and affinities. This permits the production of antibodies that bind to a selected antigen with a selected affinity. The approach of constructing synthetic single chain antibodies is directly applicable to constructing synthetic Fab fragments which can also be easily displayed and screened. The diversity of the synthetic antibody libraries can be increased by altering the chain lengths of the CDRs and also by incorporating changes in the framework regions that may affect antibody affinity. In addition, alternative libraries can be generated with varying degrees of randomness or diversity by limiting the amount of degeneracy at certain positions within the CDRs. The synthetic binding site can be modified further by varying the chain lengths of the CDRs and adjusting amino acids at defined positions in the CDRs or the framework region which may affect affinities. Antibodies identified from the synthetic antibody library can easily be manipulated to adjust their affinity and or effector functions. In addition, the synthetic antibody library is amenable to use in other combinatorial type approaches. Also, nucleic acid amplification techniques have made it possible to engineer humanized antibodies and to clone the immunoglobulin (antibody) repertoire of an immunized mouse from spleen cells into phage expression vectors and identify expressed antibody fragments specific to the antigen used for immunization (see, e.g., U.S. Pat. No. 5,395,750).

Phage-display is a versatile technique for the discovery of binding proteins. Methods have been developed for the generation and display of both random peptide loops (Burritt et al. (1996) *Anal. Biochem.* 238:1–13; Lowman (1997) *Annu. Rev. Biophys. Biomol. Struct.* 26:410–424; and Wilson et al. (1998) *Can. J. Microbiol.* 44:313–329) and antibody fragments containing the variable antigen recognition region [Fvs] (Chiswell et al. (1992) *Trends Biotechnol.* 10:80–84; Hill, et al. (1996) *Mol. Microbiol.* 20:685–692; Parmley et al. (1988) *Gene* 73:305–318). Polypeptide loops or Fvs are optionally expressed as conjugates with the gene pill coat protein of M13 phage, resulting in the display of fused proteins on the phage surface. Phage-display creates a direct linkage between the displayed polypeptide sequences and the DNA sequences that encode them, enabling rapid identification of binding peptides for an array of target proteins (see, e.g., Burritt et al. (1996) *Anal. Biochem.* 238:1–13; Chiswell et al. (1992) *Trends Biotechnol.* 10:80–84; Lowman (1997) *Annu. Rev. Biophys. Biomol. Struct.* 26:410–24; Nicola et al. (1995) *Rapid Commun. Mass Spectrom.* 9:1164–1171; and Rodi et al. (1999) *Curr. Opin. Biotechnol.* 10:87–93).

By using an in vitro "panning" process, polypeptides or Fvs that bind to a variety of targeted proteins are quickly selected (see, e.g., Burritt et al. (1996) *Anal. Biochem.* 238:1–13; Chiswell et al. (1992) *Trends Biotechnol.* 10:80–84; Hill et al. (1996) *Mol. Microbiol.* 20:685–692; Lowman (1997) *Annu. Rev. Biophys. Biomol. Struct.* 26:410–24; and Wilson 1998) *Can. J. Microbiol.* 44:313–329). Panning is carried out by incubating a library of phage-displayed polypeptides or Fvs with a surface-bound target protein, washing away the unbound phage, and eluting the specifically-bound phage. The eluted phage is then amplified, such as via infection of a host, and taken through additional cycles of panning and amplification to successively enrich the pool of phage for those with the highest affinities for the target polypeptide. After several rounds, individual clones are identified, such as by DNA sequencing, and their binding affinity and selectivity can be measured, such as by immunoassay or other suitable method (see, e.g., Fu et al. (1997) *J. Biol. Chem.* 272:25678–25684; Lowman (1997) *Annu. Rev. Biophys. Biomol. Struct.* 26:410–24; Parmley et al. (1988) *Gene* 73:305–318; and Persic et al. (1999) *FEBS Lett.* 443:112–116).

High-diversity phage-display libraries can be created for use herein. A successful library is one in which the diversity is generally about $10^7$ or greater, and more typically approaches $10^{10}$ (se, e.g., Ausubel et al. (1987) *Current Protocols in Molecular Biology*, John Wiley & Sons, New York). Methods for creating high-diversity phage-display libraries are known (see, Fu et al. (1997) *J. Biol. Chem.* 272:25678–25684; Griffiths et al. (1994) *EMBO J.* 13:3245–60; Hill et al. (1996) *Mol. Microbiol.* 20:685–692; and Persic et al. (1999) *FEBS Lett.* 443:112–116). In addition, a number of phage-display kits are commercially available that involve the use of random polypeptide loops (e.g., kits available from New England BioLabs, MA, Bio 101, CA, and Maxim Biotech, CA).

For example, random peptide loop libraries involve the use of randomized oligonucleotide synthesis to create a coding cassette in which about 5 to about 15 amino acids are randomized (see, e.g., Burritt et al. (1996) *Anal. Biochem.* 238:1–13; Lowman (1997) *Annu. Rev. Biophys. Biomol. Struct.* 26:410–24; Wilson (1998) *Can. J. Microbiol.* 44:313–329). These random polypeptide segments are optionally placed within a constraining protein structure or motif so that the loops achieve specific structures, and are not just purely random coils (see, e.g., Hill, et al. (1996) *Mol. Microbiol.* 20:685–692).

Displayed antibody fragment (Fv) libraries commonly derive their diversity from nature. The complex V-gene regions that are responsible for antibody diversity in higher vertebrates can be amplified using PCR techniques. Most approaches create a single chain antibody fragment (scFv) containing varied combinations of heavy chain (VH) and light chain (VL) sequences. Different methods for mixing, matching, and shuffling VH and VL sequences in vitro, as well as varying the cellular source of the amplified sequences, such as, but are not limited to, stem cells, tissue extracts, sera, hybridomas, and other such sources, influence the level of diversity and potential biases within a given library. These diversified polypeptide sequences, if desired can be conjugated to another protein, such as the gene pill protein of M13 phage, and between 1 and 5 copies of a given recombinant antibody are optionally displayed per phage (see, e.g., Chiswell et al. (1992) *Trends Biotechnol.* 10:80–84; Fu et al. (1997) *J. Biol. Chem.* 272:25678–25684; Parmley et al. (1988) *Gene* 73:305–318; and Persic et al. (1999) *FEBS Lett.* 443:112–116).

Random peptide loops and scFvs can be used in selecting and binding a number of different targets. Although scFvs may be capable of binding a greater variety of protein targets (see, et al. Hill, et al. (1996) *Mol. Microbiol.* 20:685–692), both methods are can be used in the methods provided herein. Proteins identified by phage-display are can be produced in large quantities either as soluble proteins or in a phage-displayed form, thus creating a renewable antibody reagent (see, e.g., Chiswell et al. (1992) *Trends Biotechnol.* 10:80–84; Fu et al. (1997) *J. Biol. Chem.* 272:25678–25684; and Persic et al. (1999) *FEBS Lett.* 443:112–116). In an exemplary embodiment, at least two peptides or scFvs that bind non-competitively to each target protein are identified and selected, such as for use in a two antibody sandwich assay (e.g., step A in FIG. 1). One exemplary method of identification and selection is described below.

Virtually any phage-display technique or library can be used in the signal detection methods used herein. For example, the method is easily adapted using methods well known to those of skill in the art to work with a variety of display systems such as *E. coli* flagellin fusion displays or T7 phage-display. For detection, the affinity recognition of a target protein is linked to or associated with a predetermined marker component, such as signature polypeptide or nucleic acid molecule encoding a signature peptide.

2) Phage and Other Display Methods for Generating and Displaying Moieties that Specifically Bind to Target Polypeptides In this embodiment, antibodies, fragments thereof or other such binding moieties are employed for specific binding to target polypeptides. This method provides a high level of flexibility and selectivity because antibodies can be selected for virtually any target or mixture of target polypeptides. For example, a plurality of bio-displayed components displaying selective antibodies for about 100 different target proteins can be used. In addition, antibodies can be used to identify particular functional forms of a given target protein, including pre- and post-processed forms, active and inactive forms, presence of modifications, such as for example, phosphorylation and glycosylation, conformational changes, and the presence of protein-ligand interactions. Multiple antibodies are optionally used, such as by displaying them on a genetic package(s) to provide a detailed functional and structural map of a given target polypeptide, such as, for example, by epitope mapping.

In one exemplary embodiment, the methods are based on immunological detection using antibody-antigen recognition of the target polypeptides and can be practiced using phage-displayed antibodies. The target polypeptide is the antigen in such a system, and an antibody or fragment thereof that recognizes and binds to the target polypeptide is used as the polypeptide binding component.

The use of phage-displayed antibodies provides several advantages, such as the use of a broad range of in vivo and in vitro selection methodologies to maximize the likelihood of producing desired antibodies and an efficient link to an amplification scheme in a suitable host, such as in a bacterial host. For example, the use of in-vitro, phage panning selection methods allows for automation and parallel processing, thus promoting an efficient development cycle in which hundreds of antibodies are optionally screened simultaneously. Phage-displayed antibodies possess a direct linkage between the displayed antibody sequence and the DNA sequences encoding them, thus enabling rapid monitoring of the binding target polypeptides via detection and quantitation of their associated DNA codes, e.g., through a predetermined polynucleotide marker. Phage transduction of bacteria and exponential growth of these bacteria mixtures in simple culture and be used as a method of nucleic acid amplification, facilitating the high levels of multiplexing for the methods herein.

The antigenic targets, such as the target polypeptides obtained, for example, from cells or tissues, that are used to select antibodies can be purified in intact forms of the target protein. Isolation of native, intact proteins can be laborious and quite frequently, an antibody is actually used to make purification feasible. The methods herein circumvent this requirement for purified native target polypeptides while still selecting specific antibodies against the desired antigen, e.g., a target polypeptide. The methods use synthetic polypeptides and recombinant expression systems in which proteins are optionally over-expressed within a host cell. Using standard cloning techniques, synthetic genes derived from complete or partial cDNA sequences are inserted into an expression vector creating an expression cassette (see, e.g., Ausubel et al. (1987) *Current Protocols in Molecular Biology*, John Wiley & Sons, New York) that, upon introduction into an appropriate host, drives the high level expression of the gene of interest. Isolation of recombinant, over-expressed proteins is often made possible by the fact that the protein of interest is expressed as a chimeric fusion to another protein or peptide sequence tag that facilitates direct isolation (see, e.g., Ausubel et al. (1987) *Current Protocols in Molecular Biology*, John Wiley & Sons, New York; Promega, Inc.'s "PINPOINT™ System) The PINPOINT™ System for direct isolation allows for the expression of a target protein as a biotinylated conjugate. These biotinylated proteins can be directly captured using a streptavidin-modified substrate and then directly used in panning experiments as described above.

In some cases, proteins, such as target proteins, are not expressed using recombinant cellular over-expression systems because their presence can be toxic to the host cell or can significantly disrupt the host's cellular functions. In these cases, the protein can be made synthetically or over-expressed as inactive/nontoxic partial protein fragments. These synthetic target proteins or protein fragments are then optionally used in panning as described above to identify antibodies, such as the two unique antibodies or peptides that bind non-competitively to the target polypeptides of interest.

For example, a series of different target proteins, including a mixture of isolated native proteins, biotinylated protein conjugates derived produced from encoding nucleic acid molecules, and synthetic peptides, can be used to select pairs of phage-displayed affinity proteins derived from different types of libraries. In one embodiment, protein and polypeptide targets selected for the assay development are selected from a set of proteins that are implicated in cancer or in other diseases.

For example, once target polypeptides are selected, a panning process is used to select antibodies that bind to the targets. The panning process involves attaching a protein to a solid substrate, such as a plastic dish, and blocking. A library of phage is then added and incubated. Unbound phage are removed by washing and bound phage are subsequently eluted. Recovered phage are amplified by growth in *E. coli*, and subjected to another round of the panning procedure. Finally, the phage selected to have the highest affinity for the targets are isolated, amplified, and sequenced (see, e.g., Chiswell et al. (1992) *Trends Biotechnol.* 10:80–84). Controls also can be included to exclude those phage which bind plastic, blocking agent, or the protein tags used to facilitate purification of the antigens (see, e.g., Wilson (1998) *Can. J. Microbiol.* 44:313–329).

f. Predetermined Markers

In addition to displaying a polypeptide binding component as described above, the genetic packages can contain a unique predetermined marker component. The predetermined marker components are used as a type of label for detection and therefore do not need to have a sequence relation to any of the other components. In one embodiment, a signature polypeptide used as a predetermined marker component is expressed in a bacterial host after a polypeptide binding component binds to a target polypeptide. Alternatively, the signature polypeptide is expressed on the surface of the genetic package. In other embodiments, the predetermined marker component contains a signature polynucleotide sequence that is optionally amplified prior to detection.

In one embodiment, the predetermined marker components contain a plurality of signature polypeptides that are expressed in an amplified host. A signature polypeptide can include a polypeptide sequence encoded by a DNA sequence in the genetic package that is expressed in a bacterial host or on the surface of the genetic package. For most embodiments herein, each signature polypeptide is associated with a specific polypeptide-binding component displayed by the genetic package. For example, each signature polypeptide is optionally associated with a specific antibody or antibody fragment displayed on a phage. The association between the signature polypeptide and the polypeptide binding component provides a link that correlates the amount of target protein bound to the polypeptide binding component. This link allows the signature polypeptide to be used as a signal generating element or label. Therefore, the signature polypeptide, rather than the target polypeptide or polypeptide binding component, is detected, such as by nuclear magnetic resonance spectroscopy (NMR), mass spectrometry, flow cytometry, or other detection method, and its presence and/or amount correlated to the presence and/or amount of target protein present in an initial sample.

Although a large variety of polypeptides, such as signature polypeptides, are readily expressed at high levels within a bacterial host, many are not optimal because of host toxicity, low expression levels and/or limited detection sensitivity. To produce a plurality of bio-displayed components with associated marker components, such as the signature polypeptides, combinatorial methods can be used to alleviate these problems by using them to select a repertoire of signature polypeptides.

Exemplary signature polypeptides are generally nontoxic, have similar expression kinetics, allow for substantially uniform cell growth following induction, and behave similarly in the detection system used, such as mass spectrometry. For example, hemoglobin protein optionally serves as a source polypeptide for combinatorial variance to produce a plurality of related marker components derived from hemoglobin.

Detection of target protein expression in this assay is based on the ability to detect over-expressed signature polypeptides in crude lysates or whole bacterial cells. Methods for detecting proteins in such lysates or cells are known (see, e.g., Easterling et al. (1998) *Anal. Chem.* 70:2704–2709).

To provide high throughput detection, the detection of the signature polypeptides can be multiplexed. A method for doing so herein uses signature polypeptide expression cassettes (SPECs) that are highly related. The first step in designing SPECs is selecting an inducible promoter. Any known promoter that provides efficient and high level expression of genes, such as in *E. coli* or other selected host are used. Such promoters include, for example, the lac promoter or recombinant tac promoter, which are induced by IPTG (see, e.g., Ausubel (1987) *Current Protocols in Molecular Biology*, John Wiley & Sons, New York) and the T7 promoter, which requires inclusion of the T7 RNA polymerase gene on the bacterial chromosome (see, e.g., Studier et al. (1990) *Methods Enzymol.* 185:60–89). These promoter sequences are used in numerous commercially-available and/or patented plasmid vectors (available, for example, from Promega, WI, New England BioLabs, MA, and Stratagene, CA).

The second step in the construction of SPECs is the design, randomization, and selection of highly related signature polypeptides to generate a set of highly-related polypeptides that are detectably distinct. For example, when mass spectrometry is used as the detection method, the polypeptides have masses that are clearly resolved in a mass spectrometer, when NMR is used they have distinguishing chemical shifts for detection by NMR and when fluorescence spectroscopy or other such detection method is used they have detectably different fluorescent labels, such as nanocrystals. In one exemplary embodiment, the hemoglobin β chain, which is easily over-expressed in a bacterial host, such as *E. coli* is used (see, e.g., Hoffman et al. (1990) *Proc. Natl. Acad. Sci.* 87:8521–8525; Jessen et al. (1994) *Methods Enzymol.* 231:347–64; Shen et al. (1993) *Biochemistry* 90:8108–8112; and Weicker et al. (1997) *Arch. Biochem. Biophys.* 348:337–346). Hemoglobin is easily detected, such as by mass spectrometry (see, e.g., Houston et al. (1997) *Rapid Commun. Mass Spectrom.* 11:1435–1439; Whittal et al. (1998) *Anal. Chem.* 70:5344–5347); and the gene encoding the hemoglobin β chain is relatively small (see, e.g., Hoffman (1990) *Proc. Natl. Acad. Sci.* 87:8521–8525; Jessen (1994) *Methods Enzymol.* 231:347–64; Shen (1993) *Biochemistry* 90:8108–8112; Weicker et al. (1997) *Arch. Biochem. Biophys.* 348:337–346).

For example, the hemoglobin β gene is randomly mutagenized to generate a family of closely related genes that encode hemoglobin proteins of differing masses. The different hemoglobin variants can be distinguished in a variety of detection systems. For example, the resolution of mass spectrometry measurements is such that many different hemoglobin variants, including those with one amino acid change, can be resolved (see, e.g., Houston et al. (1997) *Rapid Commun. Mass Spectrom.* 11:1435–1439; Whittal etal. (1998) *Anal. Chem.* 70:5344–5347). Mutagenesis of the hemoglobin β gene is easily accomplished using standard molecular and/or genetic techniques (see, e.g., Black et al. (1996) *Methods Mol. Biol.* 57:335–49; Ausubel et al. (1987) *Current Protocols in Molecular Biology*, John Wiley & Sons, New York; and Sambrook et al. (1989) *Molecular Cloning, a Laboratory Manual*, Cold Spring Harbor Laboratory Press, Cold Spring Harbor, NY).

The third step in designing SPECs involves screening a library of mutant genes for clones that generate polypeptides the signature polypeptides, that are easily detected, such as by a sensitive in a mass spectrometer in which embodiment they have a resolvable mass. The libraries can be grown on a solid medium, and the colonies picked, e.g., to nutrient broth, such as in nutrient broth in 96-well or higher density dishes. After growth and induction of expression of the signature polypeptides, such as, for example, mutant hemoglobins produced as described above, the cultures can be analyzed, such as by the selected detection method, such as by mass spectrometry. Colonies that yield a polypeptide with a robust signal and, for mass spectrometric analysis resolvable mass, are subjected to further analysis.

SPECs for multiplex detection and quantitation, such as in a mass spectrometer, can be subcloned into a phage-display genome to test the effect of inducing signature polypeptide over-expression and the effect of the cassette on cell growth and phage genome stability. Growth rates are measured, such as under non-inducing and inducing conditions using, for example, fluorescent cell proliferation systems such as the LIVE/DEAD BacLight (Molecular Probes, OR), or a similar assay that can be performed in high throughput format, such as in 96- or 384-well dishes. Clones with acceptable growth rates under the non-inducing and inducing conditions can be tested for signature polypeptide expression. The amount of protein, such as hemoglobin produced, during a time course experiment can be determined using a standard assay, such as an ELISA assay using polyclonal antibodies directed against the protein such as hemoglobin (see, e.g., Ausubel et al. (1987) *Current Protocols in Molecular Biology*, John Wiley & Sons, New York; Bethyl Laboratories, Inc, TX). Any relative expression biases within multiplexes is monitored at the detection stage, such as by using amplifiable standards and quantitated and titrated mixtures of known phage.

These approaches are used to generate a population of mutant genes, such as hemoglobin genes, encoding signature polypeptides that are easily and clearly detected, such as for measurement and resolution by mass spectrometry. The SPECs are then introduced into a phage genome containing the gene for an appropriate polypeptide binding component, such as, for example, scFvs, thus generating bio-display probes, such as phage displayed antibodies, for the immunoabsorbent assay described above. In another embodiment, the predetermined marker components include a plurality of signature polynucleotide sequences.

As described above with respect to signature polypeptides, the signature polynucleotides do not have to have, and generally do not have, any sequence relationship to the target polypeptide. The signature polynucleotide is a nucleic acid molecule or fragment that is contained within the bio-display component, such as integrated into a phage genome. Each signature polynucleotide is associated with or correlated with a specific polypeptide-binding component and their identity is known or can be known. They are used as signature markers that can be directly detected or amplified prior to detection. Amplification can be effected using PCR, host infection, electroporation, or the like. Detection of signature polynucleotides or the encoded protein can be correlated with the amount of target polypeptide in a sample.

2. Practice of the Methods a. Contacting a Sample with a Bio-Displayed Component After a plurality of genetic packages containing predetermined marker components and displaying polypeptide binding components has been chosen and prepared, the genetic packages are used to contact the target polypeptides, i.e., polypeptides of interest, such as cancer related proteins, with the polypeptide binding components. The target polypeptides are contacted by the bio-displayed components, which bind specifically to one or more of the target polypeptides. After binding of the genetic packages to the target polypeptides, the predetermined marker components in the genetic packages are used to detect the presence and/or amount of the target polypeptides.

In the methods herein, a sandwich assay can be used. In such assays, the polypeptide targets are captured by polypeptide binding components, such as, for example, antibodies, antibody fragments, scFv molecules, ligands, and other protein-binding moieties, which are attached to a solid substrate. Such substrates include, but are not limited to, one or more beads or particles, microspheres, a surface of a tube or plate, a filter membrane, and other solid supports known to those of skill in the art.

When performing traditional ELISAs, protein targets are fixed by some mechanism to the surface of a plate or beads (see, e.g., Ausubel et al. (1987) *Current Protocols in Molecular Biology*, John Wiley & Sons, New York). This is often accomplished by direct attachment of the protein target to the plastic wells of microtiter dishes or to beads. For the methods herein, for example, the solid substrate can be a plurality of agarose beads disposed within one or more microwell in a multiwell plate.

The cells and other sources containing the target polypeptides can be lysed and the target polypeptides captured onto the solid substrate. The solid substrate generally is washed to remove any unbound components. In one embodiment, the substrate contains a plurality of antibodies attached to beads. The cells are lysed and the target polypeptides in the cells bind to the antibodies on the beads. This approach has several advantages. First, sensitivity is improved when using antibodies to capture target protein for presentation (see, e.g., Ausubel et al. (1987) *Current Protocols in Molecular Biology*, John Wiley & Sons, New York) because it leads to a significant enrichment and concentration of the target polypeptide. Second, because the assay can entail the multiplexed detection of a number of different polypeptide targets, beads provide a greater surface area, thus improving binding and efficient removal of contaminating cellular proteins and debris during washing (see, e.g., Fu et al. (1997) *J. Biol. Chem.* 272:25678–25684; Lowman (1997) *Annu. Rev. Biophys. Biomol. Struct.* 26:410–24; Rivera et al. (1987) *Vet. Microbiuol.* 15:1–9; and Tijssen et al. (1991) *Curr. Opin. Immunol.* 3:233–237).

The attachment of polypeptide binding components, such as scFvs, to a solid substrate, such as a plurality beads, is a straightforward procedure. For example, many phage-display systems include an amber stop codon between the scFv gene and the phage tail gene pIII (wee, e.g., Chiswell et al. (1992) *Trends Biotechnol.* 10:80–84). In an *E. coli* host, a fusion protein that allows presentation of the scFv on a phage tail protein can be synthesized. In a strain that recognizes the amber stop codon, however, a soluble non-fused form of the scFv is synthesized. To facilitate purification, the scFv is tagged to direct the protein to the periplasm for a one-step purification (see, e.g., Fu et al. (1997) *J. Biol. Chem.* 272:25678–25684). Alternatively, it is expressed as a fusion to poly-histidine facilitating subsequent purification by affinity chromatography (see, e.g., Persic et al. (1999) *FEBS Lett.* 443:112–116). The desired scFv gene can be cloned into an expression vector for purification (see, e.g., Chiswell et al. (1992) *Trends Biotechnol.* 10:80–84; Fu et al. (1997) *J. Biol. Chem.* 272:25678–25684; and Persic et al. (1999) *FEBS Lett.* 443:112–116). Because expression is effected in bacteria, milligrams of the scFv can be produced. Finally, the purified scFvs are conjugated to the beads and used for the polypeptide target presentation.

Conjugation of purified polypeptide binding components, such as, for example, antibodies, to a solid substrate, such as, for example a plurality of beads in microwells, can be accomplished by any of the variety of methods known to those of skill in the art, including, for example, cross-linking to agarose or acrylamide beads (Lowman (1997) *Annu. Rev. Biophys. Biomol. Struct.* 26:410–24; Rivera et al. (1987) *Vet. Microbiuol.* 15:1–9), biotinylation (Fu et al. (1997) *J. Biol. Chem.* 272:25678–25684) and conjugation to streptavidin coated beads (Rivera et al. (1987) *Vet. Microbiuol.* 15:1–9), with commercially-available chemical cross-linking agents (see, e.g., Filippini et al. (1998) *Cytometry* 31:180–6; and, Tijssen et al. (1991) *Curr. Opin. Immunol.* 3:233–7; Pierce Chemical Company, IL) and any other suitable agent.

To demonstrate the effectiveness of the antigen presentation protocol, a number of target protein antigens are elected for which commercial antibodies are available, such as from Bethyl laboratories, Inc, TX. The binding can be performed on a large scale and monitored using a standard ELISA (see, e.g., Ausubel et al. (1987) *Current Protocols in Molecular Biology*, John Wiley & Sons, New York). In this manner, the binding procedure is can be tested prior to the present assay.

After the polypeptide targets are captured by the polypeptide binding component-coated substrate, such as antibody coated beads, a multiplexed mixture of bio-display probes, displaying a second polypeptide binding molecule, such as second antibody directed against the protein targets, is added to each assay module, such as each well in a microwell plate. The bio-display probes are used to bind the second polypeptide binding component to the target polypeptide, thus forming a sandwich, such as a two-antibody sandwich as shown in step A of FIG. 1.

The binding of the bio-display probes to the target polypeptide-bead complexes is proportional to the amount of each target polypeptide that has been captured in the previous step (see, e.g., Chiswell et al. (1992) *Trends Biotechnol.* 10:80–84; and Persic et al. (1999) *FEBS Lett.* 443:112–116). The solid support, such as beads, is then washed to remove all unbound phage. The wash step optionally can be optimized to maximize retention of specifically bound bio-display probes, such as genetic packages, while minimizing nonspecific binding of bio-display probes.

The bound probes can be removed from the solid substrate for further analysis, particularly detection of the predetermined markers. Removal can be accomplished by any suitable method known to those of skill in the art, such as by treatment with dilute acid, followed by neutralization (Fu et al. (1997) *J. Biol. Chem.* 272:25678–25684) or with triethylamine (Chiswell et al. (1992) *Trends Biotechnol.*

10:80–84). This step can be optimized to ensure reproducible and quantitative recovery of the genetic packages from the solid substrate.

The binding of the genetic packages to the target polypeptides attached to the solid substrate can be monitored independently using methods well known to those of skill in the art, such as sing an antibody directed against M13 phage (e.g., New England BioLabs, MA) and a standard ELISA (see, e.g., Ausubel et al. (1987) *Current Protocols in Molecular Biology*, John Wiley & Sons, New York).

Once eluted from the solid substrate, the genetic packages or the predetermined markers associated with the genetic packages are amplified as described below. The predetermined marker components from the genetic packages are then used to detect and quantify target protein expression and/or function of the target polypeptides, such as from samples containing treated or untreated cells grown, for example in 96-well plates.

b. Exemplary Amplification Techniques

After contacting and binding one or more polypeptide binding component displayed on a genetic package to one or more target polypeptide in a sample, the bound genetic packages are released or eluted from the target polypeptide. For example, they are removed from a solid substrate to which the target polypeptides were bound, such as via an antibody. The genetic packages, if desired, can then be amplified. Amplification can be accomplished in bacterial host, for example, to produce one or more amplified genetic packages. In one embodiment, a predetermined polypeptide marker in the genetic package is over expressed in the bacterial host. Alternatively, a predetermined polynucleotide marker component within the genetic package is amplified.

In one embodiment, the predetermined marker components are used to detect the target polypeptides using a highly multiplexed amplification system, such as one that takes advantage of transduction and growth. For example, bacteriophage transduction and plasmid transformation of bacteria are optionally utilized as a method for amplifying highly multiplexed mixtures of nucleic acids. Methods, such as screening cDNA libraries to provide a statistical mRNA expression profile, are dependent on the relatively unbiased nature of amplification by growth in bacteria. The use of cDNA growth and cloning has provided substantial evidence that polyclonal plasmid growth within bacteria is optionally used to amplify a mixture of clones and, under the right conditions, maintain their relative abundance levels. These methods are therefore optionally used to amplify the predetermined marker components in a genetic package in a manner that is proportional to the amount of polypeptide target bound to the bio-displayed component on the genetic package.

For example, antibodies functionally displayed on M13 phage are directly linked to specific and unique nucleic acid sequences (i.e., the M13 genome) which can be quickly amplified following infection of an *E. coli* host by the M13 phage. Other types of cells may be used, such cells include, but are not limited to, *Streptomyces, Actinomyces, Bacillus, Pseudomonas*, and other such bacterial host. This step can be used in a phage-displayed antibody selection process and can be adapted for use in a phage-based antibody detection assay as described herein. In addition, the phagemids derived from the M13 genome also can be modified, as described above, and used to force the host to over-express a defined signature polypeptide, facilitating subsequent detection of the signature polypeptides, such as by mass spectrometry.

Plasmid-based protein expression vectors are commonplace and are frequently used as a vehicle for over-expressing selected polypeptides or proteins within a bacterial host. Dozens of expression vectors are commercially available. The over-expression of a pre-determined small signature polypeptide can be inked with a phage, such as M13, sequence that encodes the display of a selected antibody. Along with the codes necessary for replication and infection, the phage-derived vector contains sequences used for the expression of both polypeptides, with the antibody generally expressed and displayed only in the phage itself and the pre-determined signature peptide expressed only in an amplifying bacterial host. Alternatively, the signature polypeptide is expressed on the surface of a phage. For example, modified coat proteins, such as, for example, P8 and P3, can be used to provide signature polypeptides that are expressed on the surface of a phage, such as an M13 phage. The signature coat polypeptides can be directly detected to provide an analysis of the target polypeptides.

To generate a signal for detection, such as by mass spectrometry, NMR and fluorescence, the DNA associated with each of the bio-display components, e.g., phage probes displaying polypeptide binding components, recovered from the binding step described can be amplified, such as by growth in a bacterial host, e.g., *E. coli*. For example, the eluted phage are mixed with a concentrated small volume of $F^+$ *E. coli* host, such as in 6-well or higher density plates (see, e.g., Smith, G. P., http://www.biosci.missouri.edu/smithgp/AmplifyingLibrary.doc). After an incubation to allow phage adsorption, a small volume of nutrient broth is added and the culture is agitated to facilitate phage probe DNA replication in the multiplying host. After this incubation, the media is supplemented with an antibiotic and an inducer (see, e.g., Fu et al. (1997) *J. Biol. Chem.* 272). The phage probe genomes also can contain a gene encoding resistance to the antibiotic to allow for selective growth of those bacterial cells that maintain the phage probe DNA which provides for unbiased growth (see, e.g., Burritt et al. (1996) *Anal. Biochem.* 238:1–13).

The amplification of the genetic package, such as in a bacterial host, may be optimized in a variety of ways. For example, the amount of bacteria added to the assay material, such as in microwells, can be in vast excess of phage probes recovered from the binding step thereby ensuring quantitative transduction of the phage genome (see, e.g., Smith, http://www.biosci.missouri.edu/smithgp/AmplifyingLibrary.doc). The efficiency of transduction optionally can be measured when phage are selected. Amplification or growth provides for expansion of the multiplexed phage probe genomes without biasing the population of clones (see, e.g., Smith, http://www.biosci.missouri.edu/smithgp/AmplifyingLibrary.doc)). Growth of cDNA libraries has been demonstrated to contain clones in ratios representative of the ratios of the transcripts in the cells from which the library was derived (see, e.g., Fannon (1996) *Trends Biotechnol.* 14:294–298; Kozian et al. (1999) *Trends Biotechnol.* 17:73–78; and Vasmatzis et al.(1998) *Proc. Natl. Acad. Sci. U.S.A.* 95:300–304). To minimize the risk of bias developing during the amplification step, the phage probe genomes can be constructed to be identical except for those regions that are different for the signature polypeptide or polynucleotide and the displayed polypeptide binding component, such as, for example, the small variable portions of scFvs (see, e.g., Griffiths et al. (1994) *EMBO J.* 13:3245–3260).

The amplification step amplifies the genetic package genomes, such as phage genomes, allowing for over-expression of the associated signature polypeptide. As well as encoding a gene for the polypeptide binding component, which can be displayed on the tail protein of the phage, the genome of each phage also encodes a specific signature polypeptide expression cassette (SPEC). The design and development of these SPECs is discussed in detail above. In brief, these cassettes contain an inducible promoter and a sequence encoding a signature polypeptide of a defined mass, followed by a termination codon. These signature polypeptides will be readily over-expressed following addition of the appropriate inducer. They are generally selected to be non-toxic to the cell and easily detected in whole bacterial cells, such as by mass spectrometry. The relative amount of protein target present in the initial cell lysate generated as described above is then correlated to the relative amount of the unique signature polypeptide assigned to that target. To make this possible, signature polypeptides have one or more detectably different characteristic, such as a unique chemical shift, mass, fluorescent label, or other characteristic, for detection and quantitation, but are similar enough to ensure that each signature peptide is expressed in the host with similar efficiency. To assess the presence of bias in the multiplexed amplification step, a population of phage can be cloned and sequenced to determine the relative abundance levels of phage versus target protein or the signature component, that is, the signature polypeptide or signature polynucleotide can be probed (see e.g., Ausubel et al. (1987) *Current Protocols in Molecular Biology*, John Wiley & Sons, New York; Brent et al. (1987) *Current Protocols in Molecular Biology*, John Wiley & Sons, New York; and Sambrook et al. (1989) *Molecular Cloning, a Laboratory Manual*, Cold Spring Harbor Laboratory Press, Cold Spring Harbor, NY).

In other embodiments, the predetermined marker component contains a polynucleotide sequence, such as, for example, in the phage genome, associated with each polypeptide binding component. After binding a genetic package to a target polypeptide, the predetermined polynucleotide sequence for each genetic package that bound to a target polypeptide is amplified for detection and quantitation.

Signature polynucleotides are optionally amplified using any one of a variety of techniques known to those of skill in the art. Any amplification methods may be used. Such methods for amplifying signature polynucleotides, include in vitro amplification techniques, such as the polymerase chain reaction (PCR). PCR involves the use of one strand of a target nucleic acid, such as the signature protein-encoding polynucleotide, to be amplified as a template for producing a large number of complements to that sequence. Generally, two primer sequences complementary to different end segments of the complementary target sequence are used to hybridize with their respective strands of the target sequence. In the presence of polymerase enzymes and nucleoside triphosphates, the primers are extended along the target sequence by the polymerase, usually a thermostable polymerase. The extensions are melted from the target sequence by raising the temperature and the process is repeated using the additional copies of the target sequence synthesized in the preceding round of amplification. Multiple rounds of denaturation, hybridization, and extension are performed to amplify the target nucleic acid, in this case the signature protein-encoding polynucleotide or signature polynucleotide.

PCR and other amplification techniques, such as, but are not limited to, the ligase chain reaction (LCR), Qβ-replicase amplification, and other RNA polymerase mediated techniques are well known, and are, for example, described with sufficient detail to direct one of skill in the art through the process in a variety of publications and patents (e.g., Sambrook et al. (1989) *Molecular Cloning, a Laboratory Manual*, Cold Spring Harbor Laboratory Press, Cold Spring Harbor, NY; Ausubel (1987) *Current Protocols in Molecular Biology*, John Wiley & Sons, New York), as well as U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3:81–94; Kwoh et al. (1989) *Proc. Natl. Acad. Sci. USA* 86:1173; Guatelli et al. (1990) *Proc. Natl. Acad. Sci. USA* 87:1874; Lomell et al. (1989) *J. Clin. Chem* 35:1826; Landegren et al. (1988) *Science* 241:1077–1080; Van Brunt (1990) *Biotechnology* 8:291–294; Wu et al. (1989) *Gene* 4:560; Barringer et al. (1990) *Gene* 89:117; and Sooknanan et al. (1995) *Biotechnology* 13:563–564).

Once the over-expressed signature polypeptides, signature polynucleotides, or amplified signature polynucleotides are obtained, they can be detected. The presence and amount of each signature component can be determined and correlated with the amount of each target polypeptide. Detection, such as by mass spectrometry and NMR, is described in more detail below, and can be performed using any suitable detection method.

c. Detection of the Polypeptides and Proteins of Interest

A variety of detection methods are known to those of skill in the art. Any such method can be used to detect the predetermined marker components obtained and prepared as described above. Such methods include, but are not limited to, performing mass spectrometry, NMR spectroscopy, hybridization, microarray detection, protein array detection, immunodetection, electrophoretic detection, surface plasmon resonance, electrochemical detection, fluorescent detection, chemiluminescent detection, colorimetric detection, electrochemiluminescent detection, and other methods known to those of skill in the art determined based upon the disclosure herein.

For example, mass spectrometry is among the methods provided herein for detecting proteins. Mass spectrometry can be coupled to protein isolation or segregation methods, such as high performance liquid chromatograph (HPLC), and used to analyze complex mixtures of proteins (see, e.g., Opiteck et al. (1998) *Anal. Biochem.* 258:349–61; and Woo et al. (1994) *Clin. Lab. Med.* 14:459–71 for mass spectrometric protein analysis methods). Direct mass measurements can be used to monitor protein modifications, such as phosphorylation or glycosylation. Because of the complexity of the samples to be analyzed, direct visualization methods using mass spectrometry are relatively slow, and the data are challenging to analyze (see, e.g., Arnott et al. (1998) *Anal. Biochem.* 258:1–18; and Opiteck et al. (1998) *Anal. Biochem.* 258:349–61).

In one embodiment, mass spectrometry (MS), which is widely used for quantitative analysis, is used to quantitate the predetermined markers. A mass spectrometer is an analytical instrument that is used to determine the molecular weights of various substances, including polypeptides and polynucleotides. In some instances, it can be used to determine the sequence of a polynucleotide or polypeptide, such as a signature polynucleotide or a signature polypeptide, and/or the chemical composition of virtually any material. A mass spectrometer generally includes a sample inlet, an ionization source, a mass analyzer, and a detector. A sample, such as a mixture of signature polypeptides, is introduced via various inlets, such as, for example via gas chromatograph (GC) or liquid chromatography (LC). The sample is then ionized to form one or more ions, which are introduced into and manipulated by the mass analyzer. Surviving ions are detected based on mass to charge ratio. Mass spectrometry techniques are well known, and, for example, described generally in *Kirk-Othmer Encyclopedia of Chemical Technology*, Volume 15, Forth Edition, pages 1071–1094, and all references therein; see also, *Mass Spectrometry for Biotechnology*, G Siuzdak, Academic Press, San Diego, Calif., 1996; *Electrospray Ionization Mass Spectrometry: Fundamentals, Instrumentation, and Applications*, R. Cole (Ed.), Wiley and Sons, 1997; *Mass Spectrometry for Chemists and Biochemists*, Johnstone et al. (1996) Cambridge University Press; *Mass Spectrometry: Principles and Applications*; Hoffman et al. (1990) *Proc. Natl. Acad. Sci.* 87:8521–8525; Wiley and Sons; *Quadrupole Mass Spectrometry and its Applications*, Dawson (ed.), Springer Verlag, 1995; and *Advances in Mass Spectrometry*, Karjalainen et al. (eds.), Elsevier Science, 1998.

GC-MS and LC-MS (MS with gas and liquid chromatography introduction) techniques are standard methods in environmental testing, and in clinical and pharmacology labs. In addition, various physical chemical reference data scales have been constructed using quantitative mass spectrometric measurements. Although differences exist in the ionization efficiencies of different molecules in the mass spectrometer, the use of proper calibration and internal standards allows these techniques to be highly reliable.

For example, sensitivity in the low femtomole range can be routinely achieved, though there have been published examples in which mid-to-low-attomole levels of peptides can be detected by MALDI (see, e.g., Li et al. (1994) *Rapid Commun. Mass Spectrom.* 8:743–749; and Solouki et al. (1995) *Anal. Chem.* 67:4139–4144). MALDI spectra of proteins and peptides from single cells have been obtained, further demonstrating the high sensitivity achievable by mass spectrometry detection (see, e.g., Whittal et al. (1998) *Anal. Chem.* 70:5344–5347; Jimenez et al. (1998) *Exp. Nephrol.* 6:421–428; and Garden et al. (1996) *J. Mass Spectrom.* 31:1126–1130).

Among the advantages of mass spectrometry as a detection method for a high throughput assay, is its capability to achieve very high levels of multiplexing in which many components are detected simultaneously. Mixtures of small peptides, e.g., hundreds of signature peptides, plus an internal standard can be analyzed concurrently, and quantitated using the methods herein. Large mixtures, including mixtures containing one hundred or more components, can be analyzed by mass spectrometry. With a source of hundreds of closely related peptides or proteins, as provided by the signature polypeptides, a highly multiplexed system results. Mass spectrometry can concurrently detect hundreds of signature polypeptides in a mixture.

An additional advantage of MALDI analysis of peptides and proteins is the high tolerance of the method to buffers and other contaminating components from crude biological samples. For example, 1 microliter crude whole blood samples, upon dilution and mixing with MALDI matrix, yield strong signals in a mass spectrometer for the subunits of hemoglobin. Normal and mutant beta-chains based on their mass differences using a delayed extraction MALDI time-of-flight (TOF) instrument have been detected (Houston et al. (1997) *Rapid Commun. Mass Spectrom.*, 11:1435–1439).

In addition, mutant hemoglobin beta chains from a single red blood cell have been detected by MALDI-TOF analysis (see, e.g. Whittal et al. (1998) *Anal. Chem.* 70:5344–5347; and Easterling et al. (1998) *Anal. Chem.* 70:2704–2709, demonstrating monitoring of protein expression in whole bacterial cells by MALDI-TOF MS). For small proteins, it is only necessary to pellet the cells, resuspend them in solvent, and mix the suspension with matrix to yield very strong signals for over-expressed proteins after induction. In order to achieve a strong mass spectrometric signal for a larger protein at 50 kDa, it was necessary to first sonicate the cells and also to rinse the dried MALDI samples with deionized water. When the time course of expression after induction was monitored, an increase in the signal of the induced protein relative to background cell proteins was observed, indicating that quantitation is possible, even from crude cell extracts.

MALDI can be used for monitoring protein expression patterns in mammalian cell culture (see, e.g., Van Adrichem et al. (1998) *Anal. Chem.* 70:923–930). Mass spectra from the direct MALDI measurement of cell pellets after lysis by a freeze-thaw cycle have been obtained. When the time course of expression of IgG light chain by a transfected CHO cell line was monitored by MALDI-TOF (24 kDa), a quantitative correlation with the values obtained by HPLC was observed. Hence quantitative analysis of proteins obtained, for example, from crude cell extracts, is feasible with MALDI.

Although generally performed using a variety of conditions and methods, the mass spectrometry detection methods provide a simple method of concurrent detection for tens to hundreds of signature polypeptides or signature polynucleotides. Although routine experimentation may be needed to determine the best conditions for a particular assay, the method is a simple procedure for those of skill in the art.

For example, a small aliquot of culture broth is optionally removed, diluted and mixed with a common matrix in solution, such as dihydroxybenzoic acid, sinapinic acid or ferulic acid, and spotted on a mass spectrometer sample plate. This plate is used to analyze proteins, such as a library of hemoglobin beta-chain variants that are produced in the assay. A polycrystalline film method of sample preparation can be used (see e.g., Xiang et al. (1994) *Rapid Commun. Mass Spectrom.* 8:199–204), in which samples are mixed with a matrix solution and spotted on top of a polycrystalline film of matrix. This method has been employed by others (see, e.g., Easterling et al. (1998) *Anal. Chem.* 70:2704–2709) and can be used in the present assays.

In other embodiments, the signal level is increased, such as by pelleting the cells and resuspending them in matrix solution. Alternatively, other simple purifying methods are used to prepare the samples for analysis. Based on published reports, it is usually unnecessary to subject the samples to any kind of extensive purification procedure prior to analysis in the mass spectrometer. If any type of sample clean-up is required, it is generally no more elaborate than rinsing dried MALDI samples with deionized water, a rapid and simple step that is easily automated.

In other embodiments, detection based on fluorescence, phosphorescence, radioactivity, chemiluminescence, electrochemiluminescence, an other detectable moieties, is used to detect the predetermined marker components, such as the over-expressed signature polypeptides or amplified signature polynucleotides.

Detectors for detecting labeled components are well known to those of skill in the art. For example, a radioactive label is detected using a scintillation counter or autoradiography. A fluorescent label moiety is detected by exciting the fluorophore with an appropriate wavelength of light and detecting the resulting fluorescence. For example, a fluorescent detector measures the amount of light emitted from a fluorescently labeled marker component when it is exposed to the wavelength of light at which it fluoresces. The polypeptides or polynucleotides are optionally labeled with a fluorescent moiety, such as, for example, fluorescein, fluorescein analogs, BODIPY-fluorescein, arginine, rhodamine-B, rhodamine-A, rhodamine derivatives, green fluorescent protein (GFP), and other detectable moieties. For example, the signature polypeptides are optionally labeled with the same fluorescent marker and subsequently separated, such as by electrophoresis, and detected using a fluorescent detector. Alternatively, detectably different markers are used to detect a variety of signature polypeptides. The selection and use of fluorescent label moieties and fluorescence techniques are well known (see, e.g., (1996) *Handbook of Fluorescent Probes and Research Chemicals*, by Richard P. Haugland, Sixth Edition, Molecular Probes).

In some embodiments, nanocrystals, such as semiconductor nanocrystals or quantum dots, such as cadmium selenide and cadmium sulfate, are used as fluorescent probes. One advantage nanocrystals offer to the multiplexed scheme is that they emit light in multiple colors, which allows them to be used to label and detect several biological markers simultaneously. Therefore, mixtures of predetermined markers can be detected concurrently using nanocrystals (see, e.g., Bruchez et al. (1998) *Science* 281:2013–2016).

For electrochemical detection, markers include, for example, electroactive species. For chemiluminescent detection, chemiluminescent moieties are incorporated into the predetermined marker components. UV absorption is also a detection method, for which UV absorbers are optionally used. Phosphorescent or calorimetric dyes and radioactive labels can be added to the predetermined marker components using techniques well known to those of skill, such as after amplification and/or expression, and used to detect the signature molecules.

In other embodiments, electrophoresis is used to separate the predetermined marker components based on mass/charge ratio. The components are then detected, such as by autoradiography, protein labeling and/or staining techniques. Such detection methods are well known to those of skill in the art.

Nuclear magnetic resonance (NMR) spectroscopy can be used to detect the predetermined marker components. The signature polypeptides or polynucleotides can be separated prior to NMR detection, such as by electrophoresis or HPLC. Alternatively, a mixture of signature polypeptides or polynucleotides, such as all the markers from one sample, is detected. To detect the markers in a mixture, each predetermined marker is elected to have a distinctive chemical shift that is easily distinguished in a spectrum obtained from the mixture of components, e.g., a 1D, 2D or 3D NMR spectrum. Many methods for inducing magnetic resonance, such as using various pulse sequences, detecting the signals generated and producing images from the signals are known and readily apparent to those of skill in the art (see, e.g., *Modern NMR Techniques for Chemistry Research*, by Andrew Derome, (Pergamon Press 1987); and *NMR in Physiology and Biomedicine*, by Robert Gillies, (Academic Press, 1994) for reviews of magnetic resonance principles; see, e.g., *Spectroscopic Identification of Organic Compounds*, Fourth Edition, by Silverstein et al. (John Wiley and Sons, New York, 1981); and *Organic Spectroscopy*, by Brown et al. (1988) John Wiley and Sons, New York, for information on chemical shifts of various types of molecules).

Hybridization is also an optional method of detection. Hybridization of a labeled probe to a predetermined marker component is performed using methods well known to those of skill in the art. The hybridization is followed by detection of the labeled probe, such as, for example, by fluorescence, radioactivity or chemiluminescence. For example, hybridization can be used to detect signature nucleic acids directly from phage or post amplification signature polynucleotides. Such hybridization detection can be performed using microarray technology. For example, oligonucleotides complementary to the signature polynucleotides described above are said to form an array to which the signature polynucleotides, such as labeled signature polynucleotides, are hybridized. Alternatively, a set of receptors that bind to the signature polypeptides are used to form an array, for example by depositing the receptors on a solid surface in an array format with each receptor occupying a unique location. The over-expressed signature polypeptides are then applied to the array of receptors, incubated, and washed to remove non-binding components, and detected, such by using a label attached to either the receptors or the polypeptides. For example, each signature polypeptide is labeled with a fluorescent moiety that is detected using a fluorescent detector which monitors light emitted from the fluorescent moieties bound to the array and records a hybridization pattern. Because the identity and position of each array member is known, the identity of the target polypeptides or polynucleotides bound to each position can be determined. Arrays can contain any desired number of polypeptides or polynucleotides, such as about 10,000 or more polypeptides or polynucleotides deposited on a support, such as a glass surface, thereby providing multiplexed analysis by allowing a mixture of predetermined marker components to be concurrently detected. Array technology is well known to those of skill (see, e.g., (2000) *Microarray Biochip Technology*, by Mark Schena, Eaton Pub. Co; (1999) *DNA Microarrays: A Practical Approach*, by Mark Schena, Oxford Univ. Press; Fodor (1997), "Genes, Chips and the Human Genome," *FASEB Journal* 11:A879, 1997; Fodor (1997) "Massively Parallel Genomics," *Science* 277:393–395; and Chee et al. (1996) *Science* 274:610–614; and many other patents and publications known and available to those of skill in this art).

In other embodiments, surface plasmon resonance is used to detect the predetermined markers. Surface plasmon resonance (SPR) detects bimolecular interactions in real time using light reflected off of a thin metal film. An SPR response reflects a change in mass concentration at a detector surface as molecules bind or dissociate from a sensor chip. Target molecules can be immobilized, such as on a thin metal film, and then contacted with ligands, such as for example, in a mobile phase flowed through a flow cell. If binding of the ligand to a target on the surface occurs, the local refractive index changes, producing a change in the SPR angle, which is monitored by detecting changes in intensity of the reflected light. The size of the SPR change is directly proportional to the mass being immobilized and thus is useful in quantitating the amount of each target molecule bound to ligand. A mixture of predetermined markers correlating to the target polypeptides in a sample is optionally immobilized on a thin metal film and then exposed to various ligands known to bind to the predetermined markers. The markers are then detected and correlated with target polypeptides in the sample as described above. SPR devices are manufactured by Biacore, such as the Biacore 1000 and Biacore 2000, (Uppsala Sweden).

c. Integrated Assay Systems

The detection schemes described can be integrated with various other components to provide a high-throughput, fully automated, multiplexed system. For example, an assay module and a robotic handler are optionally combined with a detection system to integrate the assay into an automated process.

The above methods of assaying target polypeptides, for expression level and/or functionality, can be automated in a high throughput integrated system. For example, the processes described above, each as a stand-alone component, such as, for example, phage panning, sandwich immunoassays, inoculation of cultures, and detection, such as mass spectrometric spotting procedures, can be automated into an integrated high throughput system that analyzes target polypeptide mixtures, containing about 10 to 100 or more polypeptides, directly from cellular extracts. For example, a majority of the processes can be performed robotically.

One embodiment of an integrated assay system includes a solid support containing one or more target polypeptides. A robotic sample handler can be used to contact the solid support with a plurality of bio-displayed polypeptide binding components. For example, a pipetting robot is optionally used to dispense a plurality of genetic packages, containing predetermined markers and displaying polypeptide binding components, into a plurality of microwells containing a plurality of beads. The target polypeptides in this example are attached to the beads in the microwells. The polypeptide binding components bind to one or more of the one or more target polypeptides as described above. In addition, each polypeptide binding component is associated with a different marker component, such as a signature polypeptide. Unbound polypeptide binding components are washed from the solid support, with a sample handler, such as a pipetting robot that dispenses and removes a wash solution from a plurality of microwells.

An assay module integrated with the solid support is then used, to amplify and/or express the marker component. As described above, after binding to the target polypeptides, the bio-display components are released from the solid support and amplified. Alternatively, the marker component within the bio-display component is amplified. Such amplifications are carried out in an automated manner in the present system, such as by using a sample processing platform equipped with robotic sample handlers and pipetting robots. For example, the assays can be performed in microwell plates on a platform containing robotic handlers that remove the bio-display components from a plurality of beads before dispensing the bio-display component into a microwell for amplification.

Once amplified, a robotic sample handler is used to prepare the samples for detection in a detection module, such as, for example, by spotting dried samples onto a plate for mass spectrometric (MS) analysis. The marker components within the samples are then detected in the detection module, which detects one or more different marker components concurrently in a single sample, and determines an amount of the one or more different marker component in the sample. The sample is automatically introduced into the detection module, such as with an automatic injector that injects a different sample into the detection module, which can be performed at predetermined specific intervals.

The detection module can be in operational communication with an analyzing module. The analyzing system can include a computer or computer readable medium containing one or more instruction set for correlating an amount of each different marker component with the one or more target polypeptide. Examples of integrated systems are provided below.

In one embodiment of a high throughput integrated system, high-throughput sample processing platforms are used (see, e.g. Hawkins (1997) *Science* 276:1887–1889) Commercially available automation and robotics equipment also can used and/or adapted to create a high throughput system (available from companies, such as CRS Robotics, Burlington, Ontario; and Packard Instruments Company, Inc., Meriden Conn.). Various platforms are used to, for example, process samples in 96-well or loci, 384-well or loci, 1536-well loci and higher density plate or solid substrate formats. For example, the systems optionally integrate a single-tip Beckman BioMek pipetting robot, one or more 96-tip MultiMek robot (Beckman), plate hotels, plate washers, incubators, thermal cyclers, other small equipment and Sagian robotic arms for moving microtiter trays. The assay modules, such as the individual modules as described above, are integrated and performed in a high throughput format using various combinations of these elements.

Devices for assay automation include, for example, a single tip BioMek, a 96-tip MultiMek, and a 96-well multi-solution plate washer. These can be combined with other devices and procedures developed for mass spectrometric analyses for procedures, such as reagent addition, bead capture, bead wash, elution of samples from beads, and spotting of samples on conductive plates for mass spectrometric analysis (see, e.g., U.S. Pat. No. 6,104,028, entitled "Volatile Matrices for Matrix-assisted Laser Desorption/ionization Mass Spectrometry," by Hunter et al.; U.S. Pat. No. 6,090,558, entitled "DNA Typing by Mass Spectrometry with Polymorphic DNA Repeat Markers," by Butler et al.; U.S. Pat. No. 6,051,378, entitled "Methods of Screening Nucleic Acids Using Mass Spectrometry," by Monforte et al.; U.S. Pat. No. 5,965,363, entitled "Methods of Preparing Nucleic Acids for Mass Spectrometric Analysis," by Monforte et al.; and U.S. Pat. No. 5,864,137, entitled "Mass Spectrometer," by Becker et al.). Flow-through and top wash approaches optionally are used, such as for procedures involving beads as a solid substrate. Each process, including phage panning, sandwich immunoassays, inoculation of cultures, and detection,such as mass spectrometric spotting procedures, is treated as an automated component or "module" and any or all modules in the process can be automated, such as in a single integrated system.

A high throughput, scanning MALDI-TOF mass spectrometer provides one example of a detection system that is easily integrated into the multiplexed systems. Mass spectrometry systems that process large numbers of samples without the need for exchanging sample plates are known and available. Multiple sample trays of standard microtiter plate dimensions are processed in an uninterrupted fashion. Sample densities start at about 384 samples per plate, up to about 1,536 samples and higher. Since mass spectrometers generally scan through and analyze samples serially, the overall analysis time is a multiple of the per-sample analysis time. Analysis of small peptides is straightforward and per-sample analysis time can average about 1 to about 3 seconds per sample, providing an expected throughput of about 1,200 to about 3,600 samples per system, per hour (independent of multiplexing). When multiplexing is performed as described above, each sample contains a mixture of signature polypeptides, therefore providing a higher throughput for signature polypeptide detection. For example, if each sample contains about 20 polypeptides, then the multiplexed assay described above detects about 24,000 to about 72,000 polypeptides in about an hour, thereby providing a high throughput assay system.

A fully automated system as described above takes a plurality of samples and contacts them with a plurality of genetic packages containing predetermined marker components associated with polypeptide binding components. The polypeptide binding components bind to target polypeptides in the sample and the marker components are used to detect the target polypeptides.

After detection of the predetermined marker components, such as the amplified signature polynucleotides, an analysis module, such as a computer, in operational communication with the detection system is used for data analysis, such as correlating the amount of each target polypeptide in the sample with the amount of predetermined marker component detected. For example, the analysis module optionally calculates a ratio of a first marker component to a second marker component and optionally correlates that ratio to the ratio of a first and second target polypeptide in the sample that was assayed. The ratios are determined from the data obtained by the detection system, which generates a plurality of data points based, for example, on the amount and/or identity of each marker component. The data points are used in the analysis module, in which a computer or computer readable medium, containing one or more instruction set for organizing data points into a database, compiles the data points into a database containing a profile for each sample or each target polypeptide in a sample. The profiles can identify an expression level and a functional state for each target polypeptide in the sample. The instructions sets used to compile such profiles can include software for generating a graphical representation of the amount of each polypeptide. In addition, the instruction sets associated with the analysis module optionally include software for performing statistical analysis, such as, for example, multivariate analysis, principle component analysis, or difference analysis, on the plurality of data points. In addition, the software and the instruction sets can produce an output file embodied in a computer readable medium, which output file can include the profiles described above.

For example, a mass spectrometry system or other detection system, as described above, can run in a fully automatic fashion including an analysis module. All data analysis, signal detection and assessment, as well as general instrument control, can use automated routines embedded into controlling hardware and software. The use of a load-lock system means that exchange times can be only about 5 minutes when cycling multiple sample plates, minimizing down time between runs. Data can be analyzed in real time using algorithms that, in the case of polypeptides, detect peaks, remove background, and measure peak areas and intensities. Data can be downloaded, such as via a 100BT ethernet to server warehouses. Raw data is converted to genomic data and stored in a data base, such as an Oracle database. For example, samples are tracked through production facilities using the Baan ERP (Enterprise Resource Planning) system and the Beckman SAMI LIMS (Laboratory Information Management Systems) system. In addition, other bioinformatic tools for the analysis of complex information can be employed.

While the foregoing has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. Since modifications will be apparent to those of skill in this art, it is intended that this invention be limited only by the scope of the appended claims.

What is claimed is:

1. A multiplexed method of detecting a plurality of target polypeptides in a sample composition, the method comprising:
   a) contacting the sample composition with genetic packages that each display a polypeptide-binding component under conditions whereby the plurality of target polypeptides in the sample form complexes with displayed polypeptide-binding components specific therefor, wherein:
      each genetic package comprises a predetermined marker component that is indicative of the displayed polypeptide-binding component; and
      the polypeptide-binding component specifically binds to at least one of the target polypeptides, whereby target polypeptides that bind thereto can be identified by virtue of the marker component; and
      wherein the genetic packages are selected from the group consisting of a bacteriophage, a virus and a bacterium;
   b) separating complexes of the plurality of target polypeptides with the displayed polypeptide-binding components on the genetic packages from the sample composition;
   c) optionally amplifying the genetic packages that have formed complexes, resulting in amplified genetic packages, or amplifying the marker components in the genetic packages that have formed complexes;
   d) identifying marker components in the genetic packages that have formed complexes, thereby detecting the plurality of target polypeptides in the sample, wherein:
      identification of a marker component is effected by mass spectrometry; and
      identification of a marker component indicates the presence of a target polypeptide in the sample.

2. The method of claim 1, wherein the target polypeptides comprise proteins, biotinylated proteins, isolated proteins, recombinant proteins, enzymes enzyme substrates cancer proteins or disease related proteins.

3. The method of claim 1, wherein target polypeptides in the sample or genetic packages in the sample are bound to a solid support.

4. The method of claim 3, wherein the solid support comprises one or more of a microsphere or bead, a surface of a tube or plate or a filter membrane.

5. The method of claim 3, further comprising washing the solid support after the polypeptide binding component specifically binds at least one of the one or more polypeptides.

6. The method of claim 1, comprising concurrently detecting at least about 10 to about $10^9$ polypeptides.

7. The method of claim 6, comprising concurrently detecting at least about 50 to about 10,000 polypeptides.

8. The method of claim 6, comprising concurrently detecting at least about 3 to about 500 polypeptides.

9. The method of claim 6, comprising concurrently detecting at least about 3 to about 100 polypeptides.

10. The method of claim 1, wherein the sample is a tissue sample, a blood sample, a cell lysate or a plurality of cultured cells.

11. The method of claim 1, wherein the virus comprises a a baculovirus.

12. The method of claim 11, wherein the bacteriophage comprises T4 phage, M13 phage or lambda phage.

13. The method of claim 1, wherein the plurality of bio-displayed polypeptide binding components comprises about $10^2$ to about $10^{10}$ different polypeptide-binding components.

14. The method of claim 1, wherein the plurality of bio-displayed polypeptide binding components comprises about $10^5$ to about $10^{10}$ different polypeptide-binding components.

15. The method of claim 1, wherein the polypeptide-binding component comprises one or more of an agent selected from among an antibody, an antibody fragment, a single chain antibody fragment, an enzyme, biotin, avidin, streptavidin, a ligand and a receptor.

16. The method of claim 15, wherein the antibody, the antibody fragment or the single chain antibody fragment comprises one or more antigen recognition regions.

17. The method of claim 1, wherein mass spectrometry format comprises matrix-assisted laser desorption/ionization (MALDI) time-of-flight (TOF) mass spectrometry.

18. The method of claim 1, further comprising determining an amount of the marker component.

19. The method of claim 18, comprising correlating the amount of the marker component to an amount of at least one of the one or more polypeptides in the sample.

20. The method of claim 1, wherein the genetic package comprises a surface and wherein the marker component comprises a nucleic acid, which nucleic acid encodes a polypeptide, which polypeptide is expressed on the surface of the genetic package.

21. The method of claim 1, wherein the predetermined marker component comprises a nucleic acid fragment.

22. The method of claim 21, wherein amplifying the marker component comprises performing polymerase chain reaction, ligase chain reaction, or Qβ-replicase amplification of the nucleic acid fragment or a detectable portion thereof.

23. The method of claim 1, wherein the genetic packages or nucleic acid molecules encoding the predeterminded marker components are amplified prior to detection of the markers.

24. The method of claim 23, wherein amplifying the genetic packages comprises performing polymerase chain reaction, ligase chain reaction, or Qβ-replicase amplification of the nucleic acid molecule encoding the predeterminded marker component or amplifying or a detectable portion of the nucleic acid molecule encoding the predeterminded maker component.

* * * * *